US012797445B2

(12) United States Patent
Shykind et al.

(10) Patent No.: US 12,797,445 B2

(45) Date of Patent: Nov. 17, 2026

(54) MODULATION OF AAV-BASED GENE EXPRESSION

(71) Applicant: Prevail Therapeutics, Inc., New York, NY (US)

(72) Inventors: Benjamin Shykind, New York, NY (US); Asa Abeliovich, New York, NY (US); E. David Litwack, New York, NY (US); Kumar Anindya Sen, Revere, MA (US)

(73) Assignee: PREVAIL THERAPEUTICS, INC., New York, NY (US)

( * ) Notice: Subject to any disclaimer, the term of this patent is extended or adjusted under 35 U.S.C. 154(b) by 535 days.

(21) Appl. No.: 18/273,845

(22) PCT Filed: Jan. 24, 2022

(86) PCT No.: PCT/US2022/013476

§ 371 (c)(1),
(2) Date: Jul. 24, 2023

(87) PCT Pub. No.: WO2022/159799

PCT Pub. Date: Jul. 28, 2022

(65) Prior Publication Data

US 2024/0100132 A1 Mar. 28, 2024

Related U.S. Application Data

(60) Provisional application No. 63/141,110, filed on Jan. 25, 2021.

(51) Int. Cl.

| | |
|---|---|
| ***A61K 38/47*** | (2006.01) |
| ***A61K 31/712*** | (2006.01) |
| ***A61K 48/00*** | (2006.01) |
| ***A61P 1/16*** | (2006.01) |
| ***C12N 15/113*** | (2010.01) |
| ***C12N 15/86*** | (2006.01) |

(52) U.S. Cl.

CPC ............ *A61K 38/47* (2013.01); *A61K 31/712* (2013.01); *A61K 48/0058* (2013.01); *A61P 1/16* (2018.01); *C12N 15/113* (2013.01); *C12N 15/86* (2013.01); *C12Y 302/01021* (2013.01); *C12N 2310/11* (2013.01); *C12N 2310/315* (2013.01); *C12N 2310/321* (2013.01); *C12N 2310/3231* (2013.01); *C12N 2310/341* (2013.01); *C12N 2750/14143* (2013.01)

(58) Field of Classification Search

None

See application file for complete search history.

(56) References Cited

U.S. PATENT DOCUMENTS

| | | | | |
|---|---|---|---|---|
| 6,468,524 | B1 | 10/2002 | Chiorini et al. | |
| 2004/0224405 | A1* | 11/2004 | Leake .................. | C12N 15/111 435/375 |
| 2010/0211327 | A1 | 8/2010 | Hahner et al. | |
| 2010/0310576 | A1* | 12/2010 | Adams .................... | A61P 25/00 435/375 |
| 2017/0037402 | A1 | 2/2017 | Esau et al. | |
| 2018/0237775 | A1* | 8/2018 | Dumonceaux ......... | C12N 15/86 |
| 2021/0015898 | A1* | 1/2021 | Mich .................... | A61K 38/177 |

FOREIGN PATENT DOCUMENTS

| | | | |
|---|---|---|---|
| EP | 1225229 | A1 | 7/2002 |
| EP | 3995571 | A1 | 5/2022 |
| WO | WO 2006/031371 | A2 | 3/2006 |
| WO | WO 2013/049493 | A1 | 4/2013 |
| WO | WO 2015/056014 | A1 | 4/2015 |
| WO | WO 2019/143885 | A1 | 7/2019 |
| WO | WO 2021/002412 | A1 | 1/2021 |

OTHER PUBLICATIONS

Xia, et al. High levels of protein expression using different mammalian CMV promoters in several cell lines. Protein Expression & Purification. 2006; 45: 115-124. (Year: 2006).*

Chan, et al. Antisense oligonucleotides: From design to therapeutic application. Clinical and Experimental Pharmacology and Physiology. 2006; 33:533-540. (Year: 2006).*

Lim and Brown. Hepatitis B virus nuclear export elements: RNA stem-loop α and β, key parts of the HBV post-transcriptional regulatory element. RNA Biology. 2016; 13(9):743-747. (Year: 2016).*

Srivastava A. Advances and challenges in the use of recombinant adeno-associated virus vectors for human gene therapy. Cell & Gene Therapy Insights. 2016; 2(5):553-575. (Year: 2016).*

Invitation to Pay Additional Fees for Application No. PCT/US2022/013476, mailed Apr. 28, 2022.

International Search Report and Written Opinion for Application No. PCT/US2022/013476, mailed Jun. 22, 2022.

International Preliminary Report on Patentability for Application No. PCT/US2022/013476, mailed Aug. 3, 2023.

Extended European Search Report for Application No. EP 22743313.3 mailed Nov. 22, 2024.

Lim et al., Antisense oligonucleotide modulation of non-productive alternative splicing upregulates gene expression. Nat Commun. Jul. 9, 2020;11(1):3501. doi: 10.1038/s41467-020-17093-9.

Zhong et al., A reversible RNA on-switch that controls gene expression of AAV-delivered therapeutics in vivo. Nat Biotechnol. Feb. 2020;38(2):169-175. doi: 10.1038/s41587-019-0357-y. Epub Dec. 23, 2019.

* cited by examiner

*Primary Examiner* — Allison M Fox
*Assistant Examiner* — Gina Pronzati
(74) *Attorney, Agent, or Firm* — Brian C. Cholewa

(57) ABSTRACT

Aspects of the disclosure relate to compositions and methods for positively or negatively regulating the expression of a gene therapeutic (e.g., a therapeutic protein expressed from an AAV vector). The disclosure is based, in part, on certain nucleic acids, for example antisense oligonucleotides (ASOs), configured to bind specific regions of an expression cassette (or an mRNA transcribed from such an expression cassette).

12 Claims, 5 Drawing Sheets

Specification includes a Sequence Listing.

PR001 with ASO binding
3935 bp

SEQUENCE LISTING

<160> NUMBER OF SEQ ID NOS: 120

<210> SEQ ID NO 1
<211> LENGTH: 141
<212> TYPE: DNA
<213> ORGANISM: Artificial Sequence
<220> FEATURE:
<223> OTHER INFORMATION: Synthetic

<400> SEQUENCE: 1
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc t 141

<210> SEQ ID NO 2
<211> LENGTH: 19
<212> TYPE: DNA
<213> ORGANISM: Artificial sequence
<220> FEATURE:
<223> OTHER INFORMATION: Synthetic

<400> SEQUENCE: 2
gcgcgcagct gcctgcagg 19

<210> SEQ ID NO 3
<211> LENGTH: 20
<212> TYPE: DNA
<213> ORGANISM: Artificial sequence
<220> FEATURE:
<223> OTHER INFORMATION: Synthetic

<400> SEQUENCE: 3
cggcctcagt gagcgagcga 20

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
acgcccgggc tttgcccggg 20

<210> SEQ ID NO 5
<211> LENGTH: 21
<212> TYPE: DNA
<213> ORGANISM: Artificial sequence
<220> FEATURE:
<223> OTHER INFORMATION: Synthetic

<400> SEQUENCE: 5
cgggcgacca aaggtcgccc g 21

<210> SEQ ID NO 6
<211> LENGTH: 20
<212> TYPE: DNA
<213> ORGANISM: Artificial sequence
<220> FEATURE:
<223> OTHER INFORMATION: Synthetic

<400> SEQUENCE: 6
gctcgctcgc tcactgaggc 20

<210> SEQ ID NO 7
<211> LENGTH: 20
<212> TYPE: DNA
<213> ORGANISM: Artificial sequence
<220> FEATURE:
<223> OTHER INFORMATION: Synthetic

<400> SEQUENCE: 7
tggccactcc ctctctgcgc 20

<210> SEQ ID NO 8
<211> LENGTH: 21
<212> TYPE: DNA
<213> ORGANISM: Artificial sequence
<220> FEATURE:
<223> OTHER INFORMATION: Synthetic

<400> SEQUENCE: 8
aggaacccct agtgatggag t 21

<210> SEQ ID NO 9
<211> LENGTH: 304
<212> TYPE: DNA
<213> ORGANISM: Artificial sequence
<220> FEATURE:
<223> OTHER INFORMATION: Synthetic

<400> SEQUENCE: 9
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catg 304

<210> SEQ ID NO 10
<211> LENGTH: 21
<212> TYPE: DNA
<213> ORGANISM: Artificial sequence
<220> FEATURE:
<223> OTHER INFORMATION: Synthetic

<400> SEQUENCE: 10
tttaccgtaa gttatgtaac g 21

<210> SEQ ID NO 11
<211> LENGTH: 21
<212> TYPE: DNA
<213> ORGANISM: Artificial sequence
<220> FEATURE:
<223> OTHER INFORMATION: Synthetic

<400> SEQUENCE: 11
ggcggtcagc caggcgggcc a 21

<210> SEQ ID NO 12

<211> LENGTH: 21
<212> TYPE: DNA
<213> ORGANISM: Artificial sequence
<220> FEATURE:
<223> OTHER INFORMATION: Synthetic

<400> SEQUENCE: 12
gtcaatgggc gggggtcgtt g 21

<210> SEQ ID NO 13
<211> LENGTH: 21
<212> TYPE: DNA
<213> ORGANISM: Artificial sequence
<220> FEATURE:
<223> OTHER INFORMATION: Synthetic

<400> SEQUENCE: 13
ggaacatacg tcattattga c 21

<210> SEQ ID NO 14
<211> LENGTH: 21
<212> TYPE: DNA
<213> ORGANISM: Artificial sequence
<220> FEATURE:
<223> OTHER INFORMATION: Synthetic

<400> SEQUENCE: 14
gtccctattg gcgttactat g 21

<210> SEQ ID NO 15
<211> LENGTH: 21
<212> TYPE: DNA
<213> ORGANISM: Artificial sequence
<220> FEATURE:
<223> OTHER INFORMATION: Synthetic

<400> SEQUENCE: 15
acccattgac gtcaatggaa a 21

<210> SEQ ID NO 16
<211> LENGTH: 21
<212> TYPE: DNA
<213> ORGANISM: Artificial sequence
<220> FEATURE:
<223> OTHER INFORMATION: Synthetic

<400> SEQUENCE: 16
gcagtttacc gtaaatactc c 21

<210> SEQ ID NO 17
<211> LENGTH: 21
<212> TYPE: DNA
<213> ORGANISM: Artificial sequence
<220> FEATURE:
<223> OTHER INFORMATION: Synthetic

<400> SEQUENCE: 17
acttgatgta ctgccaagtg g 21

<210> SEQ ID NO 18
<211> LENGTH: 21
<212> TYPE: DNA
<213> ORGANISM: Artificial sequence
<220> FEATURE:
<223> OTHER INFORMATION: Synthetic

<400> SEQUENCE: 18
ggcgtacttg gcatatgata c 21

<210> SEQ ID NO 19
<211> LENGTH: 21
<212> TYPE: DNA
<213> ORGANISM: Artificial sequence
<220> FEATURE:
<223> OTHER INFORMATION: Synthetic

<400> SEQUENCE: 19
ccgtcattga cgtcaatagg g 21

<210> SEQ ID NO 20
<211> LENGTH: 21
<212> TYPE: DNA
<213> ORGANISM: Artificial sequence
<220> FEATURE:
<223> OTHER INFORMATION: Synthetic

<400> SEQUENCE: 20
taatgccagg cgggccattt a 21

<210> SEQ ID NO 21
<211> LENGTH: 21
<212> TYPE: DNA
<213> ORGANISM: Artificial sequence
<220> FEATURE:
<223> OTHER INFORMATION: Synthetic

<400> SEQUENCE: 21
cataaggtca tgtactgggc a 21

<210> SEQ ID NO 22
<211> LENGTH: 21
<212> TYPE: DNA
<213> ORGANISM: Artificial sequence
<220> FEATURE:
<223> OTHER INFORMATION: Synthetic

<400> SEQUENCE: 22
tactgccaag taggaaagtc c 21

<210> SEQ ID NO 23
<211> LENGTH: 21
<212> TYPE: DNA
<213> ORGANISM: Artificial sequence
<220> FEATURE:
<223> OTHER INFORMATION: Synthetic

<400> SEQUENCE: 23
gcgatgacta atacgtagat g 21

<210> SEQ ID NO 24
<211> LENGTH: 19
<212> TYPE: DNA
<213> ORGANISM: Artificial sequence
<220> FEATURE:
<223> OTHER INFORMATION: Synthetic

<400> SEQUENCE: 24
ccatggtaat agcgatgac 19

<210> SEQ ID NO 25
<211> LENGTH: 278
<212> TYPE: DNA

<213> ORGANISM: Artificial sequence
<220> FEATURE:
<223> OTHER INFORMATION: Synthetic

<400> SEQUENCE: 25
tcgaggtgag ccccacgttc tgcttcactc tccccatctc cccccctcc ccaccccca 60 ttttgtattt atttattttt taattatttt gtgcagcgat gggggcgggg gggggggggg 120
ggcgcgcgcc aggcggggcg gggcggggcg aggggcgggg cggggcgagg cggagaggtg 180
cggcggcagc caatcagagc ggcgcgctcc gaaagtttcc ttttatggcg aggcggcggc 240
ggcggcggcc ctataaaaag cgaagcgcgc ggcgggcg 278

<210> SEQ ID NO 26
<211> LENGTH: 21
<212> TYPE: DNA
<213> ORGANISM: Artificial sequence
<220> FEATURE:
<223> OTHER INFORMATION: Synthetic

<400> SEQUENCE: 26
agaacgtggg gctcacctcg a 21

<210> SEQ ID NO 27
<211> LENGTH: 21
<212> TYPE: DNA
<213> ORGANISM: Artificial sequence
<220> FEATURE:
<223> OTHER INFORMATION: Synthetic

<400> SEQUENCE: 27
gggagatggg gagagtgaag c 21

<210> SEQ ID NO 28
<211> LENGTH: 21
<212> TYPE: DNA
<213> ORGANISM: Artificial sequence
<220> FEATURE:
<223> OTHER INFORMATION: Synthetic

<400> SEQUENCE: 28
aaattggggg tggggagggg g 21

<210> SEQ ID NO 29
<211> LENGTH: 21
<212> TYPE: DNA
<213> ORGANISM: Artificial sequence
<220> FEATURE:
<223> OTHER INFORMATION: Synthetic

<400> SEQUENCE: 29
attaaaaaat aaataaatac a 21

<210> SEQ ID NO 30
<211> LENGTH: 21
<212> TYPE: DNA
<213> ORGANISM: Artificial sequence
<220> FEATURE:
<223> OTHER INFORMATION: Synthetic

<400> SEQUENCE: 30
cccccatcgc tgcacaaaat a 21

<210> SEQ ID NO 31
<211> LENGTH: 21

<212> TYPE: DNA
<213> ORGANISM: Artificial sequence
<220> FEATURE:
<223> OTHER INFORMATION: Synthetic

<400> SEQUENCE: 31
cgcgcccccc cccccccccc g 21

<210> SEQ ID NO 32
<211> LENGTH: 21
<212> TYPE: DNA
<213> ORGANISM: Artificial sequence
<220> FEATURE:
<223> OTHER INFORMATION: Synthetic

<400> SEQUENCE: 32
cccgccccgc cccgcctggc g 21

<210> SEQ ID NO 33
<211> LENGTH: 21
<212> TYPE: DNA
<213> ORGANISM: Artificial sequence
<220> FEATURE:
<223> OTHER INFORMATION: Synthetic

<400> SEQUENCE: 33
tcgccccgcc ccgcccctcg c 21

<210> SEQ ID NO 34
<211> LENGTH: 21
<212> TYPE: DNA
<213> ORGANISM: Artificial sequence
<220> FEATURE:
<223> OTHER INFORMATION: Synthetic

<400> SEQUENCE: 34
ctgccgccgc acctctccgc c 21

<210> SEQ ID NO 35
<211> LENGTH: 21
<212> TYPE: DNA
<213> ORGANISM: Artificial sequence
<220> FEATURE:
<223> OTHER INFORMATION: Synthetic

<400> SEQUENCE: 35
ggagcgcgcc gctctgattg g 21

<210> SEQ ID NO 36
<211> LENGTH: 21
<212> TYPE: DNA
<213> ORGANISM: Artificial sequence
<220> FEATURE:
<223> OTHER INFORMATION: Synthetic

<400> SEQUENCE: 36
tcgccataaa aggaaacttt c 21

<210> SEQ ID NO 37
<211> LENGTH: 21
<212> TYPE: DNA
<213> ORGANISM: Artificial sequence
<220> FEATURE:
<223> OTHER INFORMATION: Synthetic

<400> SEQUENCE: 37

```
agggccgccg ccgccgccgc c                                               21


<210> SEQ ID NO 38
<211> LENGTH: 21
<212> TYPE: DNA
<213> ORGANISM: Artificial sequence
<220> FEATURE:
<223> OTHER INFORMATION: Synthetic

<400> SEQUENCE: 38

gccgcgcgct tcgcttttta t                                               21


<210> SEQ ID NO 39
<211> LENGTH: 21
<212> TYPE: DNA
<213> ORGANISM: Artificial sequence
<220> FEATURE:
<223> OTHER INFORMATION: Synthetic

<400> SEQUENCE: 39

agcgcgcagc gactcccgcc c                                               21


<210> SEQ ID NO 40
<211> LENGTH: 1611
<212> TYPE: RNA
<213> ORGANISM: Artificial sequence
<220> FEATURE:
<223> OTHER INFORMATION: Synthetic

<400> SEQUENCE: 40

auggaauuca gcagccccag cagagaggaa ugccccaagc cucugagccg ggugucaauc      60

auggccggau cucugacagg acugcugcug cuucaggccg ugucuugggc uucuggcgcu     120

agaccuugca uccccaagag cuucggcuac agcagcgucg ugugcgugug caaugccacc     180

uacugcgaca gcuucgaccc uccuaccuuu ccugcucugg gcaccuucag cagauacgag     240

agcaccagau ccggcagacg gauggaacug agcaugggac ccauccaggc caaucacaca     300

ggcacuggcc ugcugcugac acugcagccu gagcagaaau uccagaaagu gaaaggcuuc     360

ggcggagcca ugacagaugc cgccgcucug aauauccugg cucugucucc accagcucag     420

aaccugcugc ucaagagcua cuucagcgag gaaggcaucg gcuacaacau caucagagug     480

cccauggcca gcugcgacuu cagcaucagg accuacaccu acgccgacac acccgacgau     540

uuccagcugc acaacuucag ccugccugaa gaggacacca agcugaagau cccucugauc     600

cacagagccc ugcagcuggc acaaagaccc gugucacugc uggccucucc auggacaucu     660

cccaccuggc ugaaaacaaa uggcgccgug aauggcaagg gcagccugaa aggccaaccu     720

ggcgacaucu accaccagac cugggccaga uacuucguga aguuccugga cgccuaugcc     780

gagcacaagc ugcaguuuug ggccgugaca gccgagaacg aaccuucugc uggacugcug     840

agcggcuacc ccuuucagug ccugggcuuu acacccgagc accagcggga cuuuaucgcc     900

cgugaucugg gacccacacu ggccaauagc acccaccaua augugcggcu gcugaugcug     960

gacgaccaga gacugcuucu gccccacugg gcuaaagugg ugcugacaga uccugaggcc    1020

gccaaauacg ugcacggaau cgccgugcac ugguaucugg acuuucuggc cccugccaag    1080

gccacacugg gagagacaca cagacuguuc cccaacacca ugcuguucgc cagcgaagcc    1140

ugugugggca gcaaguuuug ggaacagagc gugcggcucg gcagcuggga uagaggcaug    1200

caguacagcc acagcaucau caccaaccug cuguaccacg ucgucggcug gaccgacugg    1260

aaucuggccc ugaauccuga aggcggcccu aacugggucc gaaacuucgu ggacagcccc    1320
```

aucaucgugg acaucaccaa ggacaccuuc uacaagcagc ccauguucua ccaccuggga 1380
cacuucagca aguucauccc cgagggcucu cagcgcguug gacugguggc uucccagaag 1440
aacgaucugg acgccguggc ucugaugcac ccugauggau cugcuguggu ggugguccug 1500
aaccgcagca gcaaagaugu gccccugacc aucaaggauc ccgccguggg auuccuggaa 1560
acaaucagcc cuggcuacuc cauccacacc uaccuguggc guagacagug a 1611

<210> SEQ ID NO 41
<211> LENGTH: 21
<212> TYPE: RNA
<213> ORGANISM: Artificial sequence
<220> FEATURE:
<223> OTHER INFORMATION: Synthetic

<400> SEQUENCE: 41
gcugcugaau uccauggugg c 21

<210> SEQ ID NO 42
<211> LENGTH: 21
<212> TYPE: RNA
<213> ORGANISM: Artificial sequence
<220> FEATURE:
<223> OTHER INFORMATION: Synthetic

<400> SEQUENCE: 42
ggggcauucc ucucugcugg g 21

<210> SEQ ID NO 43
<211> LENGTH: 21
<212> TYPE: RNA
<213> ORGANISM: Artificial sequence
<220> FEATURE:
<223> OTHER INFORMATION: Synthetic

<400> SEQUENCE: 43
ugacacccgg cucagaggcu u 21

<210> SEQ ID NO 44
<211> LENGTH: 21
<212> TYPE: RNA
<213> ORGANISM: Artificial sequence
<220> FEATURE:
<223> OTHER INFORMATION: Synthetic

<400> SEQUENCE: 44
ugucagagau ccggccauga u 21

<210> SEQ ID NO 45
<211> LENGTH: 21
<212> TYPE: RNA
<213> ORGANISM: Artificial sequence
<220> FEATURE:
<223> OTHER INFORMATION: Synthetic

<400> SEQUENCE: 45
ggccugaagc agcagcaguc c 21

<210> SEQ ID NO 46
<211> LENGTH: 21
<212> TYPE: RNA
<213> ORGANISM: Artificial sequence
<220> FEATURE:
<223> OTHER INFORMATION: Synthetic

<400> SEQUENCE: 46
agcgccagaa gcccaagaca c 21

<210> SEQ ID NO 47
<211> LENGTH: 21
<212> TYPE: RNA
<213> ORGANISM: Artificial sequence
<220> FEATURE:
<223> OTHER INFORMATION: Synthetic

<400> SEQUENCE: 47
gcucuugggg augcaagguc u 21

<210> SEQ ID NO 48
<211> LENGTH: 21
<212> TYPE: RNA
<213> ORGANISM: Artificial sequence
<220> FEATURE:
<223> OTHER INFORMATION: Synthetic

<400> SEQUENCE: 48
cacgacgcug cuguagccga a 21

<210> SEQ ID NO 49
<211> LENGTH: 21
<212> TYPE: RNA
<213> ORGANISM: Artificial sequence
<220> FEATURE:
<223> OTHER INFORMATION: Synthetic

<400> SEQUENCE: 49
guagguggca uugcacacgc a 21

<210> SEQ ID NO 50
<211> LENGTH: 21
<212> TYPE: RNA
<213> ORGANISM: Artificial sequence
<220> FEATURE:
<223> OTHER INFORMATION: Synthetic

<400> SEQUENCE: 50
aggagggucg aagcugucgc a 21

<210> SEQ ID NO 51
<211> LENGTH: 589
<212> TYPE: RNA
<213> ORGANISM: Artificial sequence
<220> FEATURE:
<223> OTHER INFORMATION: Synthetic

<400> SEQUENCE: 51
aaucaaccuc uggauuacaa aauuugugaa agauugacug guauucuuaa cuauguugcu 60
ccuuuuacgc uauguggaua cgcugcuuua augccuuugu aucaugcuau ugcuucccgu 120
auggcuuuca uuuucuccuc cuuguauaaa uccugguugc ugucucuuua ugaggaguug 180
uggcccguug ucaggcaacg uggcguggug ugcacugugu uugcugacgc aacccccacu 240
gguuggggca uugccaccac cugucagcuc cuuuccggga cuuucgcuuu ccccucccu 300 auugccacgg cggaacucau cgccgccugc cuugcccgcu gcuggacagg ggcucggcug 360
uugggcacug acaauuccgu gguguugucg gggaaaucau cguccuuucc uuggcugcuc 420
gccuguguug ccaccuggau ucugcgcggg acguccuucu gcuacguccc uucggcccuc 480
aauccagcgg accuuccuuc ccgcggccug cugccggcuc ugcggccucu uccgcgucuu 540
cgccuucgcc cucagacgag ucggaucucc cuuugggccg ccucccccgc 589

<210> SEQ ID NO 52
<211> LENGTH: 21
<212> TYPE: RNA
<213> ORGANISM: Artificial sequence
<220> FEATURE:
<223> OTHER INFORMATION: Synthetic

<400> SEQUENCE: 52
uuuguaaucc agagguugau u 21

<210> SEQ ID NO 53
<211> LENGTH: 21
<212> TYPE: RNA
<213> ORGANISM: Artificial sequence
<220> FEATURE:
<223> OTHER INFORMATION: Synthetic

<400> SEQUENCE: 53
accagucaau cuuucacaaa u 21

<210> SEQ ID NO 54
<211> LENGTH: 21
<212> TYPE: RNA
<213> ORGANISM: Artificial sequence
<220> FEATURE:
<223> OTHER INFORMATION: Synthetic

<400> SEQUENCE: 54
aggagcaaca uaguuaagaa u 21

<210> SEQ ID NO 55
<211> LENGTH: 21
<212> TYPE: RNA
<213> ORGANISM: Artificial sequence
<220> FEATURE:
<223> OTHER INFORMATION: Synthetic

<400> SEQUENCE: 55
agcguaucca cauagcguaa a 21

<210> SEQ ID NO 56
<211> LENGTH: 21
<212> TYPE: RNA
<213> ORGANISM: Artificial sequence
<220> FEATURE:
<223> OTHER INFORMATION: Synthetic

<400> SEQUENCE: 56
augauacaaa ggcauuaaag c 21

<210> SEQ ID NO 57
<211> LENGTH: 21
<212> TYPE: RNA
<213> ORGANISM: Artificial sequence
<220> FEATURE:
<223> OTHER INFORMATION: Synthetic

<400> SEQUENCE: 57
agccauacgg gaagcaauag c 21

<210> SEQ ID NO 58
<211> LENGTH: 21
<212> TYPE: RNA

<213> ORGANISM: Artificial sequence
<220> FEATURE:
<223> OTHER INFORMATION: Synthetic

<400> SEQUENCE: 58
auacaaggag gagaaaauga a 21

<210> SEQ ID NO 59
<211> LENGTH: 21
<212> TYPE: RNA
<213> ORGANISM: Artificial sequence
<220> FEATURE:
<223> OTHER INFORMATION: Synthetic

<400> SEQUENCE: 59
aagagacagc aaccaggauu u 21

<210> SEQ ID NO 60
<211> LENGTH: 21
<212> TYPE: RNA
<213> ORGANISM: Artificial sequence
<220> FEATURE:
<223> OTHER INFORMATION: Synthetic

<400> SEQUENCE: 60
aacgggccac aacuccucau a 21

<210> SEQ ID NO 61
<211> LENGTH: 21
<212> TYPE: RNA
<213> ORGANISM: Artificial sequence
<220> FEATURE:
<223> OTHER INFORMATION: Synthetic

<400> SEQUENCE: 61
caccacgcca cguugccuga c 21

<210> SEQ ID NO 62
<211> LENGTH: 21
<212> TYPE: RNA
<213> ORGANISM: Artificial sequence
<220> FEATURE:
<223> OTHER INFORMATION: Synthetic

<400> SEQUENCE: 62
ugcgucagca aacacagugc a 21

<210> SEQ ID NO 63
<211> LENGTH: 21
<212> TYPE: RNA
<213> ORGANISM: Artificial sequence
<220> FEATURE:
<223> OTHER INFORMATION: Synthetic

<400> SEQUENCE: 63
aaugccccaa ccaguggggg u 21

<210> SEQ ID NO 64
<211> LENGTH: 21
<212> TYPE: RNA
<213> ORGANISM: Artificial sequence
<220> FEATURE:
<223> OTHER INFORMATION: Synthetic

<400> SEQUENCE: 64
aaggagcuga cagguguggc c 21

<210> SEQ ID NO 65
<211> LENGTH: 21
<212> TYPE: RNA
<213> ORGANISM: Artificial sequence
<220> FEATURE:
<223> OTHER INFORMATION: Synthetic

<400> SEQUENCE: 65
ggggaaagcg aaagucccgg a 21

<210> SEQ ID NO 66
<211> LENGTH: 21
<212> TYPE: RNA
<213> ORGANISM: Artificial sequence
<220> FEATURE:
<223> OTHER INFORMATION: Synthetic

<400> SEQUENCE: 66
uuccgccgug gcaauaggga g 21

<210> SEQ ID NO 67
<211> LENGTH: 21
<212> TYPE: RNA
<213> ORGANISM: Artificial sequence
<220> FEATURE:
<223> OTHER INFORMATION: Synthetic

<400> SEQUENCE: 67
ggcaaggcag gcggcgauga g 21

<210> SEQ ID NO 68
<211> LENGTH: 21
<212> TYPE: RNA
<213> ORGANISM: Artificial sequence
<220> FEATURE:
<223> OTHER INFORMATION: Synthetic

<400> SEQUENCE: 68
ccgagccccu guccagcagc g 21

<210> SEQ ID NO 69
<211> LENGTH: 21
<212> TYPE: RNA
<213> ORGANISM: Artificial sequence
<220> FEATURE:
<223> OTHER INFORMATION: Synthetic

<400> SEQUENCE: 69
ggaauuguca gugcccaaca g 21

<210> SEQ ID NO 70
<211> LENGTH: 21
<212> TYPE: RNA
<213> ORGANISM: Artificial sequence
<220> FEATURE:
<223> OTHER INFORMATION: Synthetic

<400> SEQUENCE: 70
ugauuucccc gacaacacca c 21

<210> SEQ ID NO 71
<211> LENGTH: 21
<212> TYPE: RNA
<213> ORGANISM: Artificial sequence
<220> FEATURE:

<223> OTHER INFORMATION: Synthetic

<400> SEQUENCE: 71
gagcagccaa ggaaaggacg a 21

<210> SEQ ID NO 72
<211> LENGTH: 21
<212> TYPE: RNA
<213> ORGANISM: Artificial sequence
<220> FEATURE:
<223> OTHER INFORMATION: Synthetic

<400> SEQUENCE: 72
aauccaggug gcaacacagg c 21

<210> SEQ ID NO 73
<211> LENGTH: 21
<212> TYPE: RNA
<213> ORGANISM: Artificial sequence
<220> FEATURE:
<223> OTHER INFORMATION: Synthetic

<400> SEQUENCE: 73
gcagaaggac gucccgcgca g 21

<210> SEQ ID NO 74
<211> LENGTH: 21
<212> TYPE: RNA
<213> ORGANISM: Artificial sequence
<220> FEATURE:
<223> OTHER INFORMATION: Synthetic

<400> SEQUENCE: 74
auugagggcc gaagggacgu a 21

<210> SEQ ID NO 75
<211> LENGTH: 21
<212> TYPE: RNA
<213> ORGANISM: Artificial sequence
<220> FEATURE:
<223> OTHER INFORMATION: Synthetic

<400> SEQUENCE: 75
gcgggaagga agguccgcug g 21

<210> SEQ ID NO 76
<211> LENGTH: 21
<212> TYPE: RNA
<213> ORGANISM: Artificial sequence
<220> FEATURE:
<223> OTHER INFORMATION: Synthetic

<400> SEQUENCE: 76
ccgcagagcc ggcagcaggc c 21

<210> SEQ ID NO 77
<211> LENGTH: 21
<212> TYPE: RNA
<213> ORGANISM: Artificial sequence
<220> FEATURE:
<223> OTHER INFORMATION: Synthetic

<400> SEQUENCE: 77
aaggcgaaga cgcggaagag g 21

<210> SEQ ID NO 78
<211> LENGTH: 21
<212> TYPE: RNA
<213> ORGANISM: Artificial sequence
<220> FEATURE:
<223> OTHER INFORMATION: Synthetic

<400> SEQUENCE: 78
gauccgacuc gucugagggc g 21

<210> SEQ ID NO 79
<211> LENGTH: 21
<212> TYPE: RNA
<213> ORGANISM: Artificial sequence
<220> FEATURE:
<223> OTHER INFORMATION: Synthetic

<400> SEQUENCE: 79
cggggaggcg gcccaaaggg a 21

<210> SEQ ID NO 80
<211> LENGTH: 208
<212> TYPE: RNA
<213> ORGANISM: Artificial sequence
<220> FEATURE:
<223> OTHER INFORMATION: Synthetic

<400> SEQUENCE: 80
cugugccuuc uaguugccag ccaucuguug uuugccccuc ccccgugccu uccuugaccc 60
uggaaggugc cacucccacu guccuuuccu aauaaaauga ggaaauugca ucgcauuguc 120
ugaguaggug ucauucuauu cuggggggug ggguggggca ggacagcaag ggggaggauu 180
gggaagacaa uagcaggcau gcugggga 208

<210> SEQ ID NO 81
<211> LENGTH: 21
<212> TYPE: RNA
<213> ORGANISM: Artificial sequence
<220> FEATURE:
<223> OTHER INFORMATION: Synthetic

<400> SEQUENCE: 81
gcuggcaacu agaaggcaca g 21

<210> SEQ ID NO 82
<211> LENGTH: 21
<212> TYPE: RNA
<213> ORGANISM: Artificial sequence
<220> FEATURE:
<223> OTHER INFORMATION: Synthetic

<400> SEQUENCE: 82
gggaggggca aacaacagau g 21

<210> SEQ ID NO 83
<211> LENGTH: 21
<212> TYPE: RNA
<213> ORGANISM: Artificial sequence
<220> FEATURE:
<223> OTHER INFORMATION: Synthetic

<400> SEQUENCE: 83
ccagggucaa ggaaggcacg g 21

<210> SEQ ID NO 84

<211> LENGTH: 21
<212> TYPE: RNA
<213> ORGANISM: Artificial sequence
<220> FEATURE:
<223> OTHER INFORMATION: Synthetic

<400> SEQUENCE: 84
ggacaguggg aguggcaccu u 21

<210> SEQ ID NO 85
<211> LENGTH: 21
<212> TYPE: RNA
<213> ORGANISM: Artificial sequence
<220> FEATURE:
<223> OTHER INFORMATION: Synthetic

<400> SEQUENCE: 85
uuuccucauu uuauuaggaa a 21

<210> SEQ ID NO 86
<211> LENGTH: 21
<212> TYPE: RNA
<213> ORGANISM: Artificial sequence
<220> FEATURE:
<223> OTHER INFORMATION: Synthetic

<400> SEQUENCE: 86
uacucagaca augcgaugca a 21

<210> SEQ ID NO 87
<211> LENGTH: 21
<212> TYPE: RNA
<213> ORGANISM: Artificial sequence
<220> FEATURE:
<223> OTHER INFORMATION: Synthetic

<400> SEQUENCE: 87
cccccagaau agaaugacac c 21

<210> SEQ ID NO 88
<211> LENGTH: 21
<212> TYPE: RNA
<213> ORGANISM: Artificial sequence
<220> FEATURE:
<223> OTHER INFORMATION: Synthetic

<400> SEQUENCE: 88
ugcuguccug ccccacccca c 21

<210> SEQ ID NO 89
<211> LENGTH: 21
<212> TYPE: RNA
<213> ORGANISM: Artificial sequence
<220> FEATURE:
<223> OTHER INFORMATION: Synthetic

<400> SEQUENCE: 89
ugucuuccca auccuccccc u 21

<210> SEQ ID NO 90
<211> LENGTH: 21
<212> TYPE: RNA
<213> ORGANISM: Artificial sequence
<220> FEATURE:
<223> OTHER INFORMATION: Synthetic

<400> SEQUENCE: 90
ucuccccagc augccugcua u 21

<210> SEQ ID NO 91
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: may be modified by 2'-O-methyl
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: modified_base
<222> LOCATION: (16)..(20)
<223> OTHER INFORMATION: may be modified by 2'-O-methyl

<400> SEQUENCE: 91
ggggcattcc tctctgcugg 20

<210> SEQ ID NO 92
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: may be modified by 2'-O-methyl
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: modified_base
<222> LOCATION: (16)..(20)
<223> OTHER INFORMATION: may be modified by 2'-O-methyl

<400> SEQUENCE: 92
ugcagtgtca gcagcaggcc 20

<210> SEQ ID NO 93
<211> LENGTH: 20
<212> TYPE: RNA
<213> ORGANISM: Artificial sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: may be modified by 2'-O-methyl
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: modified_base
<222> LOCATION: (16)..(20)
<223> OTHER INFORMATION: may be modified by 2'-O-methyl

<400> SEQUENCE: 93
gguggagaca gagccaggau 20

<210> SEQ ID NO 94
<211> LENGTH: 20
<212> TYPE: DNA

<213> ORGANISM: Artificial sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: may be modified by 2'-O-methyl
<220> FEATURE:
<221> NAME/KEY: modified_base
<222> LOCATION: (16)..(20)
<223> OTHER INFORMATION: may be modified by 2'-O-methyl
<220> FEATURE:
<221> NAME/KEY: misc_feature
<222> LOCATION: (16)..(20)
<223> OTHER INFORMATION: phosphorothioate linkage

<400> SEQUENCE: 94
gccuucctcg ctgaaguagc 20

<210> SEQ ID NO 95
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: may be modified by 2'-O-methyl
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: modified_base
<222> LOCATION: (16)..(20)
<223> OTHER INFORMATION: may be modified by 2'-O-methyl

<400> SEQUENCE: 95
cgcagctggc catgggcacu 20

<210> SEQ ID NO 96
<211> LENGTH: 21
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: may be modified by 2'-O-methyl
<220> FEATURE:
<221> NAME/KEY: misc_feature
<222> LOCATION: (1)..(21)
<223> OTHER INFORMATION: phosphorothioate linkage
<220> FEATURE:
<221> NAME/KEY: modified_base
<222> LOCATION: (17)..(21)
<223> OTHER INFORMATION: may be modified by 2'-O-methyl

<400> SEQUENCE: 96
cuuucacaaa ttttgtaauc c 21

<210> SEQ ID NO 97
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: may be modified by 2'-O-methyl
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: modified_base
<222> LOCATION: (16)..(20)
<223> OTHER INFORMATION: may be modified by 2'-O-methyl

<400> SEQUENCE: 97
ggcautaaag cagcguaucc 20

<210> SEQ ID NO 98
<211> LENGTH: 22
<212> TYPE: RNA
<213> ORGANISM: Artificial sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: may be modified by 2'-O-methyl
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: modified_base
<222> LOCATION: (18)..(22)
<223> OTHER INFORMATION: may be modified by 2'-O-methyl

<400> SEQUENCE: 98
ccccgacaac accacggaau ug 22

<210> SEQ ID NO 99
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: may be modified by 2'-O-methyl
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: modified_base
<222> LOCATION: (16)..(20)
<223> OTHER INFORMATION: may be modified by 2'-O-methyl

<400> SEQUENCE: 99
gggccgaagg gacgtagcag 20

<210> SEQ ID NO 100
<211> LENGTH: 21
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: may be modified by 2'-O-methyl
<220> FEATURE:
<221> NAME/KEY: misc_feature
<222> LOCATION: (1)..(21)
<223> OTHER INFORMATION: phosphorothioate linkage
<220> FEATURE:
<221> NAME/KEY: modified_base
<222> LOCATION: (17)..(21)

<223> OTHER INFORMATION: may be modified by 2'-O-methyl

<400> SEQUENCE: 100
gcggggaggc ggcccaaagg g 21

<210> SEQ ID NO 101
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: may be modified by 2'-O-methyl
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: modified_base
<222> LOCATION: (16)..(20)
<223> OTHER INFORMATION: may be modified by 2'-O-methyl

<400> SEQUENCE: 101
ggcuggcaac tagaaggcac 20

<210> SEQ ID NO 102
<211> LENGTH: 20
<212> TYPE: RNA
<213> ORGANISM: Artificial sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: may be modified by 2'-O-methyl
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: modified_base
<222> LOCATION: (16)..(20)
<223> OTHER INFORMATION: may be modified by 2'-O-methyl

<400> SEQUENCE: 102
ggucaaggaa ggcacggggg 20

<210> SEQ ID NO 103
<211> LENGTH: 22
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: may be modified by 2'-O-methyl
<220> FEATURE:
<221> NAME/KEY: misc_feature
<222> LOCATION: (1)..(22)
<223> OTHER INFORMATION: phosphorothioate linkage
<220> FEATURE:
<221> NAME/KEY: modified_base
<222> LOCATION: (18)..(22)
<223> OTHER INFORMATION: may be modified by 2'-O-methyl

<400> SEQUENCE: 103
ccccccagaa tagaatgaca cc 22

<210> SEQ ID NO 104
<211> LENGTH: 19
<212> TYPE: RNA
<213> ORGANISM: Artificial sequence
<220> FEATURE:
<223> OTHER INFORMATION: Synthetic
<220> FEATURE:
<221> NAME/KEY: modified_base
<222> LOCATION: (1)..(19)
<223> OTHER INFORMATION: may be modified by 2'-O-methyl
<220> FEATURE:
<221> NAME/KEY: misc_feature
<222> LOCATION: (1)..(19)
<223> OTHER INFORMATION: phosphorothioate linkage

<400> SEQUENCE: 104
ggacaguggg aguggcacc 19

<210> SEQ ID NO 105
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: may be modified by 2'-O-methyl
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: modified_base
<222> LOCATION: (16)..(20)
<223> OTHER INFORMATION: may be modified by 2'-O-methyl

<400> SEQUENCE: 105
uguggccgtt tacgtcgccg 20

<210> SEQ ID NO 106
<211> LENGTH: 20
<212> TYPE: RNA
<213> ORGANISM: Artificial sequence
<220> FEATURE:
<223> OTHER INFORMATION: Synthetic

<400> SEQUENCE: 106
ggggcauucc ucucugcugg 20

<210> SEQ ID NO 107
<211> LENGTH: 20
<212> TYPE: RNA
<213> ORGANISM: Artificial sequence
<220> FEATURE:
<223> OTHER INFORMATION: Synthetic

<400> SEQUENCE: 107
ugcaguguca gcagcaggcc 20

<210> SEQ ID NO 108
<211> LENGTH: 20
<212> TYPE: RNA
<213> ORGANISM: Artificial sequence
<220> FEATURE:
<223> OTHER INFORMATION: Synthetic

<400> SEQUENCE: 108
gguggagaca gagccaggau 20

<210> SEQ ID NO 109
<211> LENGTH: 20
<212> TYPE: RNA
<213> ORGANISM: Artificial sequence
<220> FEATURE:
<223> OTHER INFORMATION: Synthetic

<400> SEQUENCE: 109
gccuuccucg cugaaguagc 20

<210> SEQ ID NO 110
<211> LENGTH: 20
<212> TYPE: RNA
<213> ORGANISM: Artificial sequence
<220> FEATURE:
<223> OTHER INFORMATION: Synthetic

<400> SEQUENCE: 110
cgcagcuggc caugggcacu 20

<210> SEQ ID NO 111
<211> LENGTH: 21
<212> TYPE: RNA
<213> ORGANISM: Artificial sequence
<220> FEATURE:
<223> OTHER INFORMATION: Synthetic

<400> SEQUENCE: 111
cuuucacaaa uuuuguaauc c 21

<210> SEQ ID NO 112
<211> LENGTH: 20
<212> TYPE: RNA
<213> ORGANISM: Artificial sequence
<220> FEATURE:
<223> OTHER INFORMATION: Synthetic

<400> SEQUENCE: 112
ggcauuaaag cagcguaucc 20

<210> SEQ ID NO 113
<211> LENGTH: 22
<212> TYPE: RNA
<213> ORGANISM: Artificial sequence
<220> FEATURE:
<223> OTHER INFORMATION: Synthetic

<400> SEQUENCE: 113
ccccgacaac accacggaau ug 22

<210> SEQ ID NO 114
<211> LENGTH: 20
<212> TYPE: RNA
<213> ORGANISM: Artificial sequence
<220> FEATURE:
<223> OTHER INFORMATION: Synthetic

<400> SEQUENCE: 114
gggccgaagg gacguagcag 20

<210> SEQ ID NO 115
<211> LENGTH: 21
<212> TYPE: RNA
<213> ORGANISM: Artificial sequence
<220> FEATURE:
<223> OTHER INFORMATION: Synthetic -continued

```
<400> SEQUENCE: 115

gcggggaggc ggcccaaagg g                                          21


<210> SEQ ID NO 116
<211> LENGTH: 20
<212> TYPE: RNA
<213> ORGANISM: Artificial sequence
<220> FEATURE:
<223> OTHER INFORMATION: Synthetic

<400> SEQUENCE: 116

ggcuggcaac uagaaggcac                                            20


<210> SEQ ID NO 117
<211> LENGTH: 20
<212> TYPE: RNA
<213> ORGANISM: Artificial sequence
<220> FEATURE:
<223> OTHER INFORMATION: Synthetic

<400> SEQUENCE: 117

ggucaaggaa ggcacggggg                                            20


<210> SEQ ID NO 118
<211> LENGTH: 22
<212> TYPE: RNA
<213> ORGANISM: Artificial sequence
<220> FEATURE:
<223> OTHER INFORMATION: Synthetic

<400> SEQUENCE: 118

ccccccagaa uagaaugaca cc                                         22


<210> SEQ ID NO 119
<211> LENGTH: 22
<212> TYPE: RNA
<213> ORGANISM: Artificial sequence
<220> FEATURE:
<223> OTHER INFORMATION: Synthetic

<400> SEQUENCE: 119

ccauagagcc caccgcaucc cc                                         22


<210> SEQ ID NO 120
<211> LENGTH: 19
<212> TYPE: RNA
<213> ORGANISM: Artificial sequence
<220> FEATURE:
<223> OTHER INFORMATION: Synthetic

<400> SEQUENCE: 120

ggacaguggg aguggcacc                                             19
```

MODULATION OF AAV-BASED GENE EXPRESSION

RELATED APPLICATIONS

This Application is a national stage filing under 35 U.S.C. § 371 of international PCT application PCT/US2022/013476, filed Jan. 24, 2022, which claims priority under 35 U.S.C. § 119(e) to U.S. provisional patent application, U.S. Ser. No. 63/141,110, filed Jan. 25, 2021, the entire contents of each of which are incorporated by reference herein.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jul. 17, 2023, is named P109470014US03-SEQ-KZM and is 29,845 bytes in size.

BACKGROUND

The ability to regulate the expression of a therapeutic transgene introduced into a patient via AAV transduction would transform the field of gene therapy. The biology underpinning the current viral approach to gene therapy ensures a long-term expression of the therapeutic transgene. This continuous expression of the therapeutic gene is appropriate for many indications, especially those resulting from a loss of function gene mutation in the genome of the patient. However, several scenarios exist where it would be highly desirable from a therapeutic dosing perspective, or from a safety perspective, to have the ability to turn therapeutic gene expression up or down, on or off; this invention describes multiple methods by which to achieve such control of gene expression through the use of specific ASOs.

SUMMARY

Aspects of the disclosure relate to compositions and methods for positively or negatively regulating the expression of a gene therapeutic (e.g., a therapeutic protein expressed from an AAV vector), through the use of certain nucleic acids, for example antisense oligonucleotides (ASOs). In some embodiments, methods described by the disclosure allow for modulation of gene expression from expression cassettes comprised of generic, widely-used, cis-acting DNA or RNA regulatory elements, or from expression cassettes bearing cis-acting DNA or RNA elements, through the interaction of the nucleic acids (e.g., ASOs) with elements in the expression cassette or a mRNA transcribed from such an expression cassette.

Accordingly, in some aspects, the disclosure provides a method for modulating expression of a transgene in a cell, the method comprising contacting a cell containing an rAAV vector comprising a transgene flanked by AAV inverted terminal repeats (ITRs) with one or more antisense oligonucleotides (ASOs) that specifically bind to at least one of the AAV ITRs, wherein binding of the one or more ASOs to the AAV ITR results in altered expression of the transgene relative to a cell that does not contain the one or more ASOs.

In some embodiments, each of the one or more ASOs ranges from about 10 nucleotides to about 30 nucleotides in length. In some embodiments, each of the ASOs comprises one or more chemical modification. In some embodiments, the one or more chemical modifications are selected from a nucleobase modification or a backbone modification. In some embodiments, all the nucleobases and/or the entire backbone of the ASO are modified. In some embodiments, a nucleobase modification comprises a 2'-O-methyl (2'OMe) modification. In some embodiments, a backbone modification comprises a phosphorothioate linkage. In some embodiments, an ASO comprises one or more locked nucleic acids (LNAs).

In some embodiments, an AAV ITR is an AAV2 ITR. In some embodiments, an AAV2 ITR comprises a nucleic acid sequence that is at least 90% identical to the nucleic acid sequence set forth in SEQ ID NO: 1. In some embodiments, an AAV2 ITR consists of the nucleic acid sequence set forth in SEQ ID NO: 1 or the complement thereof. In some embodiments, an ASO binds to at least three contiguous nucleotides of an AAV ITR.

In some embodiments, at least one ASO comprises a nucleic acid sequence that is at least 90% identical to the sequence set forth in any one of SEQ ID NOs: 2-8, or a complement thereof. In some embodiments, at least one ASO comprises a nucleic acid sequence that is at least 90% identical to the sequence set forth in any one of SEQ ID NOs: 2-8, or a complement thereof, and each of the at least one ASO comprises one or more chemical modification selected from a nucleobase modification or a backbone modification. In some embodiments, all the nucleobases and/or the entire backbone of the ASO are modified. In some embodiments, a nucleobase modification comprises a 2'-O-methyl (2'OMe) modification. In some embodiments, a backbone modification comprises a phosphorothioate linkage. In some embodiments, an ASO comprises one or more locked nucleic acids (LNAs).

In some embodiments, altered expression is increased expression of the transgene (e.g., increased expression relative to a cell that does not comprise the one or more ASOs). In some embodiments, altered expression is decreased expression of the transgene (e.g., decreased expression relative to a cell that does not comprise the one or more ASOs).

In some embodiments, a cell is a mammalian cell. In some embodiments, a mammalian cell is a human cell. In some embodiments, a cell is in a subject.

In some embodiments, a transgene is a therapeutic protein. In some embodiments, a therapeutic protein is β-glucocerebrosidase (GBA). In some embodiments, GBA is encoded by a codon-optimized nucleic acid sequence. In some embodiments, a transgene encoding GBA comprises the nucleic acid sequence set forth in SEQ ID NO: 40 or the complement thereof. In some embodiments, an rAAV vector comprises the nucleic acid sequences set forth in SEQ ID NOs: 1, 9, 25, 40, 51, and 80.

In some aspects, the disclosure provides a method for modulating expression of a transgene in a cell, the method comprising contacting a cell containing an rAAV vector comprising a transgene with one or more antisense oligonucleotides (ASOs) that specifically bind to a transcriptional control region sequence of the transgene, wherein binding of the one or more ASOs to the transcriptional control region sequence results in altered expression of the transgene relative to a cell that does not contain the one or more ASOs.

In some embodiments, each of the one or more ASOs ranges from about 10 nucleotides to about 30 nucleotides in length. In some embodiments, each of the ASOs comprises one or more chemical modification. In some embodiments, all the nucleobases and/or the entire backbone of the ASO are modified. In some embodiments, the one or more chemical modifications are selected from a nucleobase modification or a backbone modification. In some embodiments, a nucleobase modification comprises a 2'-O-methyl (2'OMe) modification. In some embodiments, a backbone modification comprises a phosphorothioate linkage. In some embodiments, an ASO comprises one or more locked nucleic acids (LNAs).

In some embodiments, a transcriptional control region sequence comprises an enhancer sequence and/or a promoter sequence. In some embodiments, an enhancer sequence is a cytomegalovirus (CMV) enhancer sequence and/or a promoter sequence is a chicken beta-actin (CBA) promoter sequence. In some embodiments, a CMV enhancer sequence comprises a nucleic acid sequence that is at least 90% identical to the nucleic acid sequence set forth in SEQ ID NO: 9 or the complement thereof. In some embodiments, a chicken beta-actin (CBA) promoter sequence comprises a nucleic acid sequence that is at least 90% identical to the nucleic acid sequence set forth in SEQ ID NO: 25 or the complement thereof.

In some embodiments, an ASO binds to at least three contiguous nucleotides of a transcriptional control region sequence.

In some embodiments, at least one ASO comprises a nucleic acid sequence that is at least 90% identical to the sequence set forth in any one of SEQ ID NOs: 10-24 and 26-39, or a complement thereof. In some embodiments, at least one ASO comprises a nucleic acid sequence that is at least 90% identical to the sequence set forth in any one of SEQ ID NOs: 10-24 and 26-39, or a complement thereof, and each of the at least one ASO comprises one or more chemical modification selected from a nucleobase modification or a backbone modification. In some embodiments, all the nucleobases and/or the entire backbone of the ASO are modified. In some embodiments, a nucleobase modification comprises a 2'-O-methyl (2'OMe) modification. In some embodiments, a backbone modification comprises a phosphorothioate linkage. In some embodiments, an ASO comprises one or more locked nucleic acids (LNAs).

In some embodiments, altered expression is increased expression of the transgene (e.g., increased expression relative to a cell that does not comprise the one or more ASOs). In some embodiments, altered expression is decreased expression of the transgene (e.g., decreased expression relative to a cell that does not comprise the one or more ASOs).

In some embodiments, a cell is a mammalian cell. In some embodiments, a mammalian cell is a human cell. In some embodiments, a cell is in a subject.

In some embodiments, a transgene is a therapeutic protein. In some embodiments, a therapeutic protein is β-glucocerebrosidase (GBA). In some embodiments, GBA is encoded by a codon-optimized nucleic acid sequence. In some embodiments, a transgene encoding GBA comprises the nucleic acid sequence set forth in SEQ ID NO: 40 or the complement thereof. In some embodiments, an rAAV vector comprises the nucleic acid sequences set forth in SEQ ID NOs: 1, 9, 25, 40, 51, and 80.

In some aspects, the disclosure provides a method for modulating expression of a transgene in a cell, the method comprising contacting a cell containing an rAAV vector comprising a transgene with one or more antisense oligonucleotides (ASOs) that specifically bind to a protein coding region of an mRNA transcribed from the transgene, wherein binding of the one or more ASOs to the protein coding region results in altered expression of the transgene relative to a cell that does not contain the one or more ASOs.

In some embodiments, each of the one or more ASOs ranges from about 10 nucleotides to about 30 nucleotides in length. In some embodiments, each of the ASOs comprises one or more chemical modification. In some embodiments, the one or more chemical modifications are selected from a nucleobase modification or a backbone modification. In some embodiments, all the nucleobases and/or the entire backbone of the ASO are modified. In some embodiments, a nucleobase modification comprises a 2'-O-methyl (2'OMe) modification. In some embodiments, a backbone modification comprises a phosphorothioate linkage. In some embodiments, an ASO comprises one or more locked nucleic acids (LNAs). In some embodiments, an ASO comprises a gapmer structure. In some embodiments, an ASO binds to at least three contiguous nucleotides of the protein coding region.

In some embodiments, at least one ASO comprises a nucleic acid sequence that is at least 90% identical to the sequence set forth in any one of SEQ ID NOs: 41-50, any one of SEQ ID NOs: 91-95, or any one of SEQ ID NOs: 106-110, or a complement thereof.

In some embodiments, a protein coding region encodes a β-glucocerebrosidase (GBA) protein. In some embodiments, a protein coding region comprises a nucleic acid sequence that is at least 90% identical to the nucleic acid sequence set forth in SEQ ID NO: 40 or the complement thereof.

In some embodiments, altered expression is increased expression of the transgene (e.g., increased expression relative to a cell that does not comprise the one or more ASOs). In some embodiments, altered expression is decreased expression of the transgene (e.g., decreased expression relative to a cell that does not comprise the one or more ASOs). In some embodiments, decreased expression of a transgene results from RNaseH-mediated degradation of mRNA transcripts bound by the one or more ASOs.

In some embodiments, a cell is a mammalian cell. In some embodiments, a mammalian cell is a human cell. In some embodiments, a cell is in a subject.

In some embodiments, an rAAV vector comprises the nucleic acid sequences set forth in SEQ ID NOs: 1, 9, 25, 40, 51, and 80.

In some aspects, the disclosure provides a method for modulating expression of a transgene in a cell, the method comprising contacting a cell containing an rAAV vector comprising a transgene with one or more antisense oligonucleotides (ASOs) that specifically bind to a woodchuck post-translational regulatory element (WPRE) of an mRNA transcribed from the transgene, wherein binding of the one or more ASOs to the WPRE results in altered expression of the transgene relative to a cell that does not contain the one or more ASOs.

In some embodiments, each of the one or more ASOs ranges from about 10 nucleotides to about 30 nucleotides in length. In some embodiments, each of the ASOs comprises one or more chemical modification. In some embodiments, the one or more chemical modifications are selected from a nucleobase modification or a backbone modification. In some embodiments, all the nucleobases and/or the entire backbone of the ASO are modified. In some embodiments, a nucleobase modification comprises a 2'-O-methyl (2'OMe) modification. In some embodiments, a backbone modification comprises a phosphorothioate linkage. In some embodiments, an ASO comprises one or more locked nucleic acids (LNAs).

In some embodiments, a WPRE comprises a nucleic acid sequence that is at least 90% identical to the nucleic acid sequence set forth in SEQ ID NO: 51 or the complement thereof. In some embodiments, an ASO binds to at least three contiguous nucleotides of the WPRE sequence.

In some embodiments, at least one ASO comprises a nucleic acid sequence that is at least 90% identical to the sequence set forth in any one of SEQ ID NOs: 52-79, any one of SEQ ID NOs: 96-100, or any ne of SEQ ID NOs: 111-115, or a complement thereof.

In some embodiments, altered expression is increased expression of the transgene (e.g., increased expression relative to a cell that does not comprise the one or more ASOs). In some embodiments, altered expression is decreased expression of the transgene (e.g., decreased expression relative to a cell that does not comprise the one or more ASOs).

In some embodiments, a cell is a mammalian cell. In some embodiments, a mammalian cell is a human cell. In some embodiments, a cell is in a subject.

In some embodiments, a transgene is a therapeutic protein. In some embodiments, a therapeutic protein is β-glucocerebrosidase (GBA). In some embodiments, GBA is encoded by a codon-optimized nucleic acid sequence. In some embodiments, a transgene encoding GBA comprises the nucleic acid sequence set forth in SEQ ID NO: 40 or the complement thereof. In some embodiments, an rAAV vector comprises the nucleic acid sequences set forth in SEQ ID NOs: 1, 9, 25, 40, 51, and 80.

In some aspects, the disclosure provides a method for modulating expression of a transgene in a cell, the method comprising contacting a cell containing an rAAV vector comprising a transgene with one or more antisense oligonucleotides (ASOs) that specifically bind to a polyadenylation element of an mRNA transcribed from the transgene, wherein binding of the one or more ASOs to the polyadenylation element results in altered expression of the transgene relative to a cell that does not contain the one or more ASOs.

In some embodiments, each of the one or more ASOs ranges from about 10 nucleotides to about 30 nucleotides in length. In some embodiments, each of the ASOs comprises one or more chemical modification. In some embodiments, the one or more chemical modifications are selected from a nucleobase modification or a backbone modification. In some embodiments, all the nucleobases and/or the entire backbone of the ASO are modified. In some embodiments, a nucleobase modification comprises a 2'-O-methyl (2'OMe) modification. In some embodiments, a backbone modification comprises a phosphorothioate linkage. In some embodiments, an ASO comprises one or more locked nucleic acids (LNAs). In some embodiments, an ASO comprises a gapmer structure. In some embodiments, an ASO binds to at least three contiguous nucleotides of a polyadenylation element.

In some embodiments, a polyadenylation element comprises the nucleic acid sequence set forth in SEQ ID NO: 80 or the complement thereof. In some embodiments, at least one ASO comprises a nucleic acid sequence that is at least 90% identical to the sequence set forth in any one of SEQ ID NOs: 81-90, any one of SEQ ID NOs: 101-104, or any one of SEQ ID NOs: 116-120, or a complement thereof.

In some embodiments, altered expression is increased expression of the transgene (e.g., increased expression relative to a cell that does not comprise the one or more ASOs). In some embodiments, altered expression is decreased expression of the transgene (e.g., decreased expression relative to a cell that does not comprise the one or more ASOs). In some embodiments, decreased expression of a transgene results from RNaseH-mediated degradation of mRNA transcripts bound by the one or more ASOs.

In some embodiments, the expression of the transgene is altered (i.e. increased or decreased), irrespective of the nature of the expressed transgene. In some embodiments, the one or more ASOs are delivered to the cell at the same time of transgene transfection. In some embodiments, the one or more ASOs are delivered to the cell several hours, for example 3 hours, after the cell is transfected with the plasmid comprising the rAAV vector encoding the transgene. In some embodiments, the one or more ASOs are delivered to the cell several weeks after the cell is transfected with the plasmid comprising the rAAV vector encoding the transgene.

In some embodiments, a cell is a mammalian cell. In some embodiments, a mammalian cell is a human cell. In some embodiments, a cell is in a subject.

In some embodiments, a transgene is a therapeutic protein. In some embodiments, a therapeutic protein is β-glucocerebrosidase (GBA). In some embodiments, GBA is encoded by a codon-optimized nucleic acid sequence. In some embodiments, a transgene encoding GBA comprises the nucleic acid sequence set forth in SEQ ID NO: 40 or the complement thereof. In some embodiments, an rAAV vector comprises the nucleic acid sequences set forth in SEQ ID NOs: 1, 9, 25, 40, 51, and 80.

In some aspects, the disclosure provides an isolated nucleic acid comprising the sequence set forth in any one of SEQ ID NOs: 2-8, 10-24, 26-39, 41-50, 52-79, 81-120, or a complement thereof. In some embodiments, an isolated nucleic acid comprises one or more chemical modifications. In some embodiments, the one or more chemical modifications comprises a 2'-O-methyl (2'OMe) modification, a phosphorothioate linkage, a locked nucleic acid (LNA), or any combination of the foregoing. In some embodiments, the isolated nucleic acid is an antisense oligonucleotide (ASO). In some embodiments, all the nucleobases and/or the entire backbone of the ASO are modified. In some embodiments, the isolated nucleic acid has a gapmer structure.

DETAILED DESCRIPTION

Figure 1:
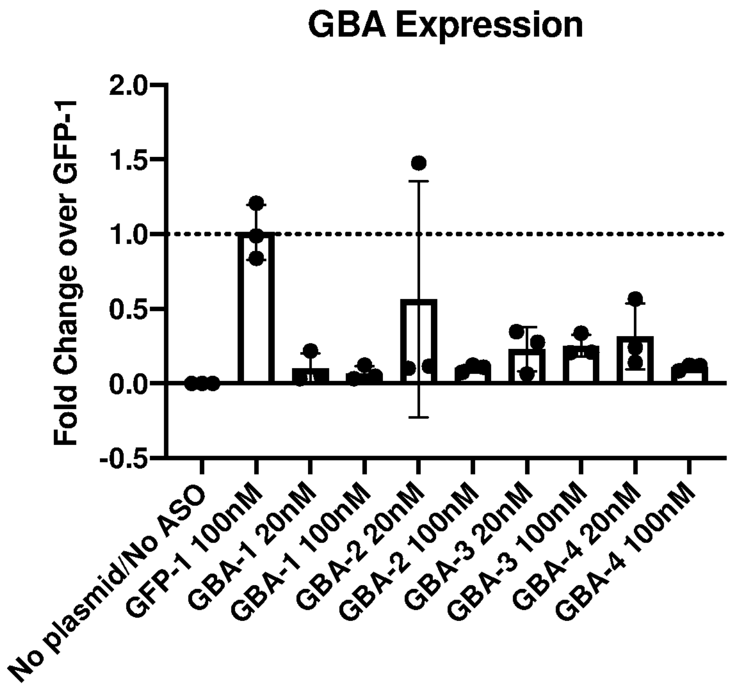
FIG. 1 shows the effects of ASOs directed against GBA on GBA expression in HEK293T cells transfected with plasmid encoding GBA and with the indicated ASO. Cells were harvested after 72 hours and GBA expression was quantified using qRT-PCR.

In some aspects, the disclosure relates to compositions and methods for modulating (e.g., positively or negatively regulating) the expression of a gene therapeutic (e.g., a therapeutic protein expressed from an AAV vector), through the use of certain nucleic acids, for example antisense oligonucleotides (ASOs). In some embodiments, nucleic acids described herein (e.g., ASOs) modulate gene expression from expression cassettes comprised of generic, widely-used, cis-acting DNA or RNA regulatory elements, from expression cassettes bearing cis-acting DNA or RNA elements, or mRNAs transcribed from such expression cassettes.

Isolated Nucleic Acids

An isolated nucleic acid may be DNA or RNA. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

The disclosure relates, in part, to isolated nucleic acids (e.g., artificial or synthetic isolated nucleic acids) comprising a region of complementarity with a target nucleotide sequence, such as a sequence from an rAAV vector, expression construct, or an mRNA transcribed from an expression construct. In some embodiments, an isolated nucleic acid is an antisense oligonucleotide (ASO).

Antisense Oligonucleotides

As used herein, the term, "antisense nucleic acid" or "ASO" refers to a nucleic acid that has sequence complementarity to a target sequence and is specifically hybridizable, e.g., under stringent conditions, with a nucleic acid having the target sequence. An antisense nucleic acid is specifically hybridizable when binding of the antisense nucleic acid to the target nucleic acid is sufficient to produce complementary based pairing between the antisense nucleic acid and the target nucleic acid, and there is a sufficient degree of complementarity to avoid non-specific binding of the antisense nucleic acid to non-target nucleic acid under conditions in which specific binding is desired, e.g., under physiological conditions in the case of in vivo assays or therapeutic treatment, and in the case of in vitro assays, under conditions in which the assays are performed. An ASO may comprise one or more DNA nucleobases, one or more RNA nucleobases, or a combination of DNA and RNA nucleobases.

Complementary refers to the capacity for precise pairing between two nucleotides. For example, if a nucleotide at a certain position of an antisense nucleic acid is capable of hydrogen bonding with a nucleotide at the corresponding position of a target nucleic acid (e.g., target nucleic acid sequence), then the antisense nucleic acid and target nucleic acid are considered to be complementary to each other at that position. The antisense nucleic acid and target nucleic acid are complementary to each other when a sufficient number of corresponding positions in each molecule are occupied by nucleotides that can hydrogen bond with each other through their bases. Thus, "complementary" is a term that is used to indicate a sufficient degree of complementarity or precise pairing such that stable and specific binding occurs between the antisense nucleic acid and target nucleic acid. However, it should be appreciated that 100% complementarity is not required. For example, in some embodiments, an antisense nucleic acid (e.g., an oligonucleotide, such as an ASO) may be at least 80% complementary to (e.g., at least 85%, 90%, 91%, 92%, 93%, 940%, 95%, 96%, 97%, 98%, 99% or 100% complementary to) the consecutive nucleotides of a target nucleic acid sequence.

In some embodiments, an antisense nucleic acid (ASO) is used that has a region of complementarity that is perfectly complementary (e.g., 100% complementary) to a portion of a target nucleic acid (e.g., a target sequence of an rAAV vector, a target sequence of an expression construct, an mRNA sequence transcribed from an expression construct, etc.). In some embodiments, an antisense nucleic acid oligonucleotide comprises a region of complementarity that is complementary with the sequence as set forth in any one of SEQ ID NO: 1, 9, 25, 40, 51, and 80. The region of complementarity of the antisense nucleic acid may be complementary with at least 3, at least 4, at least 5, at least 6, e.g., at least 7, at least 8, at least 9, at least 10, at least 15, at least 16, at least 17, at least 18, at least 19, at least 20, at least 21, at least 22, at least 23, at least 24, at least 25, or more consecutive nucleotides of a target nucleic acid sequence. In addition, to minimize the likelihood of off-target effects, an ASO may be designed to ensure that it does not have a sequence (e.g., of 5 or more consecutive nucleotides) that is complementary with an off-target nucleic acid.

However, it should be appreciated that in some embodiments, an antisense nucleic acid may be used that has less than 100% sequence complementarity with a target nucleic acid. Thus, it is understood in the art that a complementary nucleotide sequence need not be 100% complementary to that of its target to be specifically hybridizable. For example, in some embodiments, an isolated nucleic acid comprises at least 1, 2, 3, 4, 5, 6, 7, 8, 9, or 10 mismatches with its target sequence. In some embodiments, a complementary nucleic acid sequence for purposes of the present disclosure is specifically hybridizable when binding of the sequence to the target nucleic acid produces the desired alterations in gene expression (e.g., increased expression or translation of a gene product or decreased expression or translation of a gene product) to occur and there is a sufficient degree of complementarity to avoid non-specific binding to non-target nucleic acids under conditions in which avoidance of non-specific binding is desired, e.g., under physiological conditions in the case of in vivo assays or therapeutic treatment, and in the case of in vitro assays, under conditions in which the assays are performed under suitable conditions of stringency.

Sequence identity, including determination of sequence complementarity for nucleic acid sequences, may be determined by sequence comparison and alignment algorithms known in the art. To determine the percent identity of two nucleic acid sequences, the sequences are aligned for optimal comparison purposes (e.g., gaps can be introduced in the first sequence or second sequence for optimal alignment). The nucleotides at corresponding nucleotide positions are then compared. When a position in the first sequence is occupied by the same residue as the corresponding position in the second sequence, then the molecules are identical at that position. In some embodiments, the percent identity between the two sequences is a function of the number of identical positions shared by the sequences (e.g., % homology=# of identical positions/total # of positions×100), optionally penalizing the score for the number of gaps introduced and/or length of gaps introduced.

In some embodiments, oligonucleotides of the disclosure (e.g., ASOs) have a length in a range of 5 to 40 nucleotides, 5 to 30 nucleotides, 10 to 30 nucleotides, 10 to 25 nucleotides, or to 25 nucleotides. In some embodiments of the disclosure, oligonucleotides have a length of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more. In some embodiments, the oligonucleotide comprises a region of complementarity that is complementary with a region within 5, 10, 15, 25, or more nucleotides of an rAAV vector sequence, expression cassette sequence, or sequence of an mRNA transcribed from an expression cassette or rAAV vector described herein.

In some embodiments, antisense nucleic acids (e.g., oligonucleotides) are provided in a homogeneous preparation, e.g., in which at least 85%, at least 90%, at least 95%, or at least 99% of the oligonucleotides are identical. In some embodiments, a composition described by the disclosure is heterogeneous with respect to ASOs (e.g., a composition may comprise 2, 3, 4, 5, 6, 7, or more different sequences of ASOs).

Antisense nucleic acids of the disclosure may be modified to achieve one or more desired properties, such as, for example, improved cellular uptake, improved stability, reduced immunogenicity, improved potency, improved target hybridization, susceptibility to RNAse cleavage, etc. Antisense nucleic acids can be modified at a base moiety, sugar moiety and/or phosphate backbone. Accordingly, antisense nucleic acids may have one or more modified nucleotides (e.g., a nucleotide analog) and/or one or more backbone modifications (e.g., a modified internucleotide linkage). Antisense nucleic acids may have a combination of modified and unmodified nucleotides. Antisense nucleic acids may also have a combination of modified and unmodified internucleotide linkages. Antisense nucleic acids may also consist entirely of modified nucleotides and/or modified internucleotide linkages.

Antisense nucleic acids may include ribonucleotides, deoxyribonucleotides, and combinations thereof. Examples of modified nucleotides which can be used in antisense nucleic acids include, for example, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, and 2,6-diaminopurine.

In some embodiments, a modified nucleotide is a 2'-modified nucleotide. For example, the 2'-modified nucleotide may be a 2'-deoxy, 2'-fluoro, 2'-O-methyl, 2'-O-methoxyethyl, 2'-amino and 2'-aminoalkoxy modified nucleotides. In some embodiments, the 2'-modified nucleotide comprises a 2'-O-4'-C methylene bridge, such as a locked nucleic acid (LNA) nucleotide. In some embodiments of a 2' modified nucleotide the 2'-hydroxyl group is linked to the 3' or 4' carbon atom of the sugar ring thereby forming a bicyclic sugar moiety. In such embodiments, the linkage may be a methelyne $(\text{—CH2-})_n$ group bridging the 2' oxygen atom and the 3' or 4' carbon atom wherein n is 1 or 2.

Antisense nucleic acids may include combinations of LNA nucleotides and unmodified nucleotides. Antisense nucleic acids may include combinations LNA and RNA nucleotides. Antisense nucleic acids may include combinations LNA and DNA nucleotides. A further preferred oligonucleotide modification includes Locked Nucleic Acids (LNAs) in which the 2'-hydroxyl group is linked to the 3' or 4' carbon atom of the sugar ring thereby forming a bicyclic sugar moiety.

Antisense nucleic acids may also include nucleobase-modified nucleotides, e.g., nucleotides containing a non-naturally occurring nucleobase instead of a naturally occurring nucleobase. Bases may be modified to block the activity of adenosine deaminase, for example. Examples of modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

Within antisense nucleic acids (e.g., oligonucleotides) of the disclosures, as few as one and as many as all nucleotides can be modified. For example, an oligonucleotide (e.g., an oligonucleotide of 20 nucleotides in length) may contain 1, 2, 3, 4, 5, 6, 7, 8, 9, 10, 11, 12, 13, 14, 15, 16, 17, 18, 19 or 20 modified nucleotides. In some embodiments, a modified oligonucleotide will contain as few modified nucleotides as are necessary to achieve a desired level of in vivo stability and/or bioaccessibility or other desired property.

Certain antisense nucleic acids may include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain a diol, such as tetraethyleneglycol or hexaethyleneglycol, at either or both termini have also been shown to be substantially resistant to nuclease degradation and may be used herein. In some embodiments, antisense nucleic acids may include at least one lipophilic substituted nucleotide analog and/or a pyrimidine-purine dinucleotide.

In some embodiments, antisense nucleic acids (e.g., oligonucleotides) may have one or two accessible 5' ends. It is possible to create modified oligonucleotides having two such 5' ends, for instance, by attaching two oligonucleotides through a 3'-3' linkage to generate an oligonucleotide having one or two accessible 5' ends. The 3'-3'linkage may be a phosphodiester, phosphorothioate or any other modified internucleoside bridge. Additionally, 3'3'-linked oligonucleotides where the linkage between the 3' terminal nucleosides is not a phosphodiester, phosphorothioate or other modified bridge, can be prepared using an additional spacer, such as tri- or tetra-ethylenglycol phosphate moiety.

A phosphodiester internucleotide linkage of an antisense nucleic acid can be replaced with a modified linkage. The modified linkage may be selected from, for example, phosphorothioate, phosphorodithioate, NR1R2-phosphoramidate, boranophosphate, α-hydroxybenzyl phosphonate, phosphate-(C1-C21)-O-alkyl ester, phosphate-[(C6-C12) aryl-(C1-C21)-O-alkyl]ester, (C1-C8)alkylphosphonate and/or (C6-C12)arylphosphonate bridges, and (C7-C12)-α-hydroxymethyl-aryl.

A phosphate backbone of the antisense nucleic acid can be modified to generate peptide nucleic acid molecules. As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols, for example.

Antisense nucleic acids can also be formulated as morpholino oligonucleotides. In such embodiments, the riboside moiety of each subunit of an oligonucleotide of the oligonucleotide reagent is converted to a morpholine moiety. Morpholinos may also be modified, e.g. as peptide conjugated morpholino).

In other embodiments, the antisense nucleic acid (e.g., oligonucleotide) can be linked to functional groups such as peptides (e.g., for targeting host cell receptors in vivo), or agents facilitating transport across the cell membrane or the blood-brain barrier. Oligonucleotide reagents of the disclosure also may be modified with chemical moieties (e.g., cholesterol) that improve the in vivo pharmacological properties of the oligonucleotide reagents.

Aspects of the disclosure relate to ASOs having a "gapmer" structure. As used herein, "gapmer" refers to a chimeric nucleic acid sequence comprising DNA bases and RNA bases arranged as follows: (modified RNA nucleobase)$_N$-(unmodified DNA nucleobase)$_A$-(modified RNA nucleobase)$_N$, where each "N" is an integer between 1 and 20 and "A" is an integer between 2 and 10. Examples of ASOs having a "gapmer" structure include: ASOs with a "5-10-5" structure containing 5 ribonucleotides (starting from the 5' end) with 2'-O-methoxyethyl modifications, followed by 10 deoxynucleotides, followed by 5 ribonucleotides with 2'-O-methoxyethyl modifications, with all with phosphorothioate internucleotide linkages. In some embodiments, the cytidine nucleotides of a gapmer may be methylated. In some embodiments, the uridine nucleotides of a gapmer may be methylated. In some embodiments, the gapmer structure will include 15 nucleotides with alternating LNA type and deoxy-type nucleotides, all with phosphorothioate internucleotide linkages. In some embodiments, the central two nucleotides of a gapmer are deoxynucleotides. In some embodiments, an isolated nucleic acid having the sequence set forth in any one of SEQ ID NOs: 2-8, 10-24, 26-39, 41-50, 52-79, and 81-90 comprises a "gapmer" structure (the skilled artisan will recognize that in any of the nucleic acid sequences described herein, one or more "T" DNA nucleobases may be substituted with a "U" RNA nucleobase, or vice versa, in order to produce an ASO having a gapmer structure).

Nucleic Acids Targeting AAV ITRs

Aspects of the disclosure relate to methods for modulating transgene expression (e.g., transgene expression mediated by an rAAV vector or expression cassette) by contacting a cell configured to express the transgene with one or more (e.g., 1, 2, 3, 4, 5, or more) isolated nucleic acids that bind to an AAV inverted terminal repeat (ITR) (e.g., a nucleic acid sequence encoding an AAV ITR). In some embodiments, binding of an isolated nucleic acid described herein to an AAV ITR sequence increases expression of the rAAV vector containing the ITR or increases transduction efficiency of the rAAV vector containing the ITR.

An isolated nucleic acid may specifically bind to a 5' ITR, a 3' ITR, or both 5' and a 3' ITRs of an rAAV vector. In some embodiments, an isolated nucleic acid binds (e.g., hybridizes) to an AAV2 ITR. In some embodiments, an AAV2 ITR comprises or consists of the sequence set forth in SEQ ID NO: 1. In some embodiments, an isolated nucleic acid specifically binds to (e.g., hybridizes with) at least 2, 3, 4, 5, 6, 7, 8, 9, 10, 11, 12, 13, 14, 15, 16, 17, 18, 19, 20, 21, 22, 23, 24, or 25 nucleotides of an AAV2 ITR (e.g., having the sequence as set forth in SEQ ID NO: 1). In some embodiments, the isolated nucleic acids comprise or consist of the nucleic acid sequence set forth in any one of SEQ ID NOs: 2-8.

The modulation (e.g., increase or decrease) in transgene expression caused by binding of the one or more isolated nucleic acids (e.g., ASOs) to an AAV ITR may vary. In some embodiments, binding of the one or more isolated nucleic acids (e.g., ASOs) to an AAV ITR results in an increase in transgene expression of about 1%, 5%, 10%, 20%, 50%, 100%, 500%, 1000% or more, relative to transgene expression of an rAAV vector that has not been contacted with the one or more isolated nucleic acids. In some embodiments, binding of the one or more isolated nucleic acids (e.g., ASOs) to an AAV ITR results in an increase in transduction efficiency of about 1%, 5%, 10%, 20%, 50%, 100%, 500%, 1000% or more, relative to transgene expression of an rAAV vector that has not been contacted with the one or more isolated nucleic acids. In some embodiments, binding of the one or more isolated nucleic acids (e.g., ASOs) to an AAV ITR results in a decrease in transgene expression of about 1%, 5%, 10%, 20%, 50%, 100%, 500%, or 1000%, relative to transgene expression of an rAAV vector that has not been contacted with the one or more isolated nucleic acids.

Nucleic Acids Targeting Transcriptional Regulator Regions

Aspects of the disclosure relate to methods for modulating transgene expression (e.g., transgene expression mediated by an rAAV vector or expression cassette) by contacting a cell configured to express the transgene with one or more (e.g., 1, 2, 3, 4, 5, or more) isolated nucleic acids that bind to a transcriptional control region sequence (e.g., a nucleic acid sequence encoding one or more transcriptional regulators). Examples of transcriptional control region sequences include promoter sequences, enhancer sequences, repressor sequences, Kozak sequences, etc. In some embodiments, a transcriptional control region sequence comprises a promoter sequence. In some embodiments, a transcriptional control region sequence comprises an enhancer sequence. In some embodiments, binding of an isolated nucleic acid described herein to a transcriptional regulator sequence increases expression of the rAAV vector or decreases transduction efficiency of the rAAV vector.

An isolated nucleic acid may specifically bind to a promoter sequence of an rAAV vector. A promoter sequence may be a constitutive promoter sequence, inducible promoter sequence, tissue-specific promoter sequence, native promoter sequence, etc. In some embodiments, an isolated nucleic acid binds (e.g., hybridizes) to a chicken-beta actin (CBA) promoter sequence. In some embodiments, a CBA promoter sequence comprises or consists of the sequence set forth in SEQ ID NO: 9. In some embodiments, an isolated nucleic acid specifically binds to (e.g., hybridizes with) at least 2, 3, 4, 5, 6, 7, 8, 9, 10, 11, 12, 13, 14, 15, 16, 17, 18, 19, 20, 21, 22, 23, 24, or 25 nucleotides of a CBA promoter sequence (e.g., having the sequence as set forth in SEQ ID NO: 9). In some embodiments, the isolated nucleic acids comprise or consist of the nucleic acid sequence set forth in any one of SEQ ID NOs: 10-24.

An isolated nucleic acid may specifically bind to an enhancer sequence of an rAAV vector. In some embodiments, an isolated nucleic acid binds (e.g., hybridizes) to a cytomegalovirus (CMV) enhancer sequence. In some embodiments, a CMV enhancer sequence comprises or consists of the sequence set forth in SEQ ID NO: 25. In some embodiments, an isolated nucleic acid specifically binds to (e.g., hybridizes with) at least 2, 3, 4, 5, 6, 7, 8, 9, 10, 11, 12, 13, 14, 15, 16, 17, 18, 19, 20, 21, 22, 23, 24, or 25 nucleotides of a CMV promoter sequence (e.g., having the sequence as set forth in SEQ ID NO: 25). In some embodiments, the isolated nucleic acids comprise or consist of the nucleic acid sequence set forth in any one of SEQ ID NOs: 26-39.

The modulation (e.g., increase or decrease) in transgene expression caused by binding of the one or more isolated nucleic acids (e.g., ASOs) to a transcriptional control region sequence may vary. In some embodiments, binding of the one or more isolated nucleic acids (e.g., ASOs) to a transcriptional control region sequence results in an increase in transgene expression of about 1%, 5%, 10%, 20%, 50%, 100%, 500%, 1000% or more, relative to transgene expression of an rAAV vector that has not been contacted with the one or more isolated nucleic acids. In some embodiments, binding of the one or more isolated nucleic acids (e.g., ASOs) to a transcriptional control region sequence results in a decrease in transgene expression of about 1%, 5%, 10%, 20%, 50%, 100%, 500%, or 1000%, relative to transgene expression of an rAAV vector that has not been contacted with the one or more isolated nucleic acids.

Nucleic Acids Targeting Coding Sequences

Aspects of the disclosure relate to methods for modulating transgene expression (e.g., transgene expression mediated by an rAAV vector or expression cassette) by contacting a cell configured to express the transgene with one or more (e.g., 1, 2, 3, 4, 5, or more) isolated nucleic acids that bind a protein coding region (e.g., a DNA or mRNA sequence) encoding one or more therapeutic genes (e.g., a PD-associated gene), for example a Gcase (e.g., the gene product of GBA1 gene) or a portion thereof, a progranulin (e.g., the gene product of PGRN gene) or portion thereof, a prosaposin (e.g., the gene product of PSAP gene) or portion thereof, a triggering receptor expressed on myeloid cells 2 (e.g., the gene product of TREM2 gene) or a portion thereof, an apolipoprotein (e.g., the gene product of APOE gene), a C9Orf72 protein (e.g., the gene product of C9Orf72 gene) or portion thereof, etc. In some embodiments, a gene product is encoded by a coding portion (e.g., a cDNA) of a naturally occurring gene. In some embodiments, a coding region encodes a protein fragment of a natural occurring gene. A protein fragment may comprise about 50%, about 60%, about 70%, about 80% about 90% or about 99% of a naturally occurring protein. In some embodiments, a protein fragment comprises between 50% and 99.9% (e.g., any value between 50% and 99.9%) of a naturally occurring protein. In some embodiments, binding of an isolated nucleic acid described herein to a transcriptional regulator sequence decreases expression of the protein from the rAAV vector.

An isolated nucleic acid may specifically bind to a protein coding region of an rAAV vector (e.g., an mRNA transcribed from an rAAV vector). In some embodiments, an isolated nucleic acid binds (e.g., hybridizes) to a protein coding region (e.g., a DNA or mRNA sequence) encoding any one of the foregoing transgenes, or a gene product thereof, or a codon-optimized region of the transgene, or a codon-optimized region of the gene product. In some embodiments, an isolated nucleic acid binds (e.g., hybridizes) to a protein coding region encoding any one of the foregoing transgenes, or a gene product thereof, or a codon-optimized region of the transgene, or a codon-optimized region of the gene product. In some embodiments, an isolated nucleic acid binds (e.g., hybridizes) to a protein coding region that encodes β-glucocerebrosidase or GBA. Gcase, also referred to as β-glucocerebrosidase or GBA, refers to a lysosomal protein that cleaves the beta-glucosidic linkage of the chemical glucocerebroside, an intermediate in glycolipid metabolism. In humans, Gcase is encoded by the GBA1 gene, located on chromosome 1. In some embodiments, GBA1 encodes a peptide that is represented by NCBI Reference Sequence NCBI Reference Sequence NP_000148.2.

In some embodiments, an isolated nucleic acid specifically binds to a codon optimized (e.g., codon optimized for expression in mammalian cells, for example human cells) nucleic acid sequence encoding GBA protein, such as the sequence set forth in SEQ ID NO: 40. In some embodiments, an isolated nucleic acid specifically binds to (e.g., hybridizes with) at least 2, 3, 4, 5, 6, 7, 8, 9, 10, 11, 12, 13, 14, 15, 16, 17, 18, 19, 20, 21, 22, 23, 24, or 25 nucleotides of a GBA protein coding sequence (e.g., having the sequence as set forth in SEQ ID NO: 40). In some embodiments, the isolated nucleic acids comprise or consist of the nucleic acid sequence set forth in any one of SEQ ID NOs: 41-50 or any one of SEQ ID NOs: 91-95.

In some embodiments, an isolated nucleic acid that specifically binds to a protein coding region (e.g., a nucleic acid sequence encoding GBA protein, such as an mRNA sequence encoding GBA protein) comprises a gapmer structure. In some embodiments, an isolated nucleic acid having a gapmer structure comprises at least 3 contiguous nucleotides of the sequence set forth in any one of SEQ ID NOs: 41-50, any one of SEQ ID NOs: 91-95, or any one of SEQ ID NOs: 106-110.

The modulation (e.g., increase or decrease) in transgene expression caused by binding of the one or more isolated nucleic acids (e.g., ASOs) to a protein coding sequence may vary. In some embodiments, binding of the one or more isolated nucleic acids (e.g., ASOs) to a transcriptional control region sequence results in an increase in transgene expression of about 1%, 5%, 10%, 20%, 50%, 100%, 500%, 1000% or more, relative to transgene expression of an rAAV vector that has not been contacted with the one or more isolated nucleic acids. In some embodiments, binding of the one or more isolated nucleic acids (e.g., ASOs) to a protein coding sequence results in a decrease in transgene expression of about 1%, 5%, 10%, 20%, 50%, 100%, 500%, or 1000%, relative to transgene expression of an rAAV vector that has not been contacted with the one or more isolated nucleic acids.

Nucleic Acids Targeting Post-Transcriptional Regulatory Elements

Aspects of the disclosure relate to methods for modulating transgene expression (e.g., transgene expression mediated by an rAAV vector or expression cassette) by contacting a cell configured to express the transgene with one or more (e.g., 1, 2, 3, 4, 5, or more) isolated nucleic acids that bind to a post-transcriptional regulatory element sequence (e.g., a nucleic acid sequence such as an mRNA comprising a post-transcriptional regulatory element sequence). Examples of poly-adenylation element sequences include Hepatitis B virus (HPRE) and Woodchuck Hepatitis virus (WPRE), etc. In some embodiments, a post-transcriptional regulatory element sequence is a woodchuck post-transcriptional regulatory element sequence (WPRE). In some embodiments, binding of an isolated nucleic acid described herein to a post-transcriptional regulatory element sequence increases expression of the rAAV vector or decreases transduction efficiency of the rAAV vector.

An isolated nucleic acid may specifically bind to a WPRE of an rAAV vector. In some embodiments, a WPRE element sequence comprises or consists of the sequence set forth in SEQ ID NO: 51. In some embodiments, an isolated nucleic acid specifically binds to (e.g., hybridizes with) at least 2, 3, 4, 5, 6, 7, 8, 9, 10, 11, 12, 13, 14, 15, 16, 17, 18, 19, 20, 21, 22, 23, 24, or 25 nucleotides of a WPRE sequence (e.g., having the sequence as set forth in SEQ ID NO: 51). In some embodiments, the isolated nucleic acids comprise or consist of the nucleic acid sequence set forth in any one of SEQ ID NOs: 52-79, any one of SEQ ID NOs: 96-100, or any one of SEQ ID NOs: 111-115.

The modulation (e.g., increase or decrease) in transgene expression caused by binding of the one or more isolated nucleic acids (e.g., ASOs) to a post-transcriptional regulatory element sequence (e.g., WPRE) may vary. In some embodiments, binding of the one or more isolated nucleic acids (e.g., ASOs) to post-transcriptional regulatory element sequence results in an increase in transgene expression of about 1%, 5%, 10%, 20%, 50%, 100%, 500%, 1000% or more, relative to transgene expression of an rAAV vector that has not been contacted with the one or more isolated nucleic acids. In some embodiments, binding of the one or more isolated nucleic acids (e.g., ASOs) to a post-transcriptional regulatory element sequence results in a decrease in transgene expression of about 1%, 5%, 10%, 20%, 50%, 100%, 500%, or 1000%, relative to transgene expression of an rAAV vector that has not been contacted with the one or more isolated nucleic acids.

Nucleic Acids Targeting Poly-Adenylation Elements

Aspects of the disclosure relate to methods for modulating transgene expression (e.g., transgene expression mediated by an rAAV vector or expression cassette) by contacting a cell configured to express the transgene with one or more (e.g., 1, 2, 3, 4, 5, or more) isolated nucleic acids that bind to a poly-adenylation element sequence (e.g., a nucleic acid sequence such as an DNA encoding a poly-A tail or mRNA comprising a poly-U tail). Examples of poly-adenylation element sequences include SV40 poly-adenylation element, bovine growth hormone (BGH) poly-adenylation element, etc. In some embodiments, a poly-adenylation element is a BGH poly-A element. In some embodiments, binding of an isolated nucleic acid described herein to a transcriptional regulator sequence increases expression of the rAAV vector or decreases transduction efficiency of the rAAV vector.

An isolated nucleic acid may specifically bind to a BGH poly-A element of an rAAV vector. In some embodiments, a BGH poly-adenylation element sequence comprises or consists of the sequence set forth in SEQ ID NO: 80. In some embodiments, an isolated nucleic acid specifically binds to (e.g., hybridizes with) at least 2, 3, 4, 5, 6, 7, 8, 9, 10, 11, 12, 13, 14, 15, 16, 17, 18, 19, 20, 21, 22, 23, 24, or 25 nucleotides of a BGH poly-adenylation element sequence (e.g., having the sequence as set forth in SEQ ID NO: 80). In some embodiments, the isolated nucleic acids comprise or consist of the nucleic acid sequence set forth in any one of SEQ ID NOs: 81-90 or SEQ ID NOs: 101-104.

In some embodiments, an isolated nucleic acid that specifically binds to a poly-adenylation element sequence (e.g., a nucleic acid sequence encoding BGH poly-adenylation element, such as an mRNA sequence encoding a BGH poly-adenylation element) comprises a gapmer structure. In some embodiments, an isolated nucleic acid having a gapmer structure comprises at least 3 contiguous nucleotides of the sequence set forth in any one of SEQ ID NOs: 81-90, any one of SEQ ID NOs: 101-104, or any one of SEQ ID NOs: 116-120.

The modulation (e.g., increase or decrease) in transgene expression caused by binding of the one or more isolated nucleic acids (e.g., ASOs) to a BGH poly-adenylation element sequence may vary. In some embodiments, binding of the one or more isolated nucleic acids (e.g., ASOs) to a BGH poly-adenylation element sequence results in an increase in transgene expression of about 1%, 5%, 10%, 20%, 50%, 100%, 500%, 1000% or more, relative to transgene expression of an rAAV vector that has not been contacted with the one or more isolated nucleic acids. In some embodiments, binding of the one or more isolated nucleic acids (e.g., ASOs) to a BGH poly-adenylation element sequence results in a decrease in transgene expression of about 1%, 5%, 10%, 20%, 50%, 100%, 500%, or 1000%, relative to transgene expression of an rAAV vector that has not been contacted with the one or more isolated nucleic acids.

Pharmaceutical Compositions

In some aspects, the disclosure provides pharmaceutical compositions comprising an isolated nucleic acid or rAAV as described herein and a pharmaceutically acceptable carrier. As used herein, the term "pharmaceutically acceptable" refers to a material, such as a carrier or diluent, which does not abrogate the biological activity or properties of the compound, and is relatively non-toxic, e.g., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference. Compositions (e.g., pharmaceutical compositions) provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

rAAV Vectors and rAAVs

An isolated nucleic acid as described herein may exist on its own, or as part of a vector. Generally, a vector can be a plasmid, cosmid, phagemid, bacterial artificial chromosome (BAC), or a viral vector (e.g., adenoviral vector, adeno-associated virus (AAV) vector, retroviral vector, baculoviral vector, etc.). In some embodiments, the vector is a plasmid (e.g., a plasmid comprising an isolated nucleic acid as described herein). In some embodiments, an rAAV vector is single-stranded (e.g., single-stranded DNA). In some embodiments, the vector is a recombinant AAV (rAAV) vector. In some embodiments, a vector is a Baculovirus vector (e.g., an *Autographa californica* nuclear polyhedrosis (AcNPV) vector).

Typically an rAAV vector (e.g., rAAV genome) comprises a transgene (e.g., an expression construct comprising one or more of each of the following: promoter, intron, enhancer sequence, protein coding sequence, inhibitory RNA coding sequence, polyA tail sequence, etc.) flanked by two AAV inverted terminal repeat (ITR) sequences. In some embodiments the transgene of an rAAV vector comprises an isolated nucleic acid as described by the disclosure. In some embodiments, each of the two ITR sequences of an rAAV vector is a full-length ITR (e.g., approximately 145 bp in length, and containing functional Rep binding site (RBS) and terminal resolution site (trs)). In some embodiments, one of the ITRs of an rAAV vector is truncated (e.g., shortened or not full-length). In some embodiments, a truncated ITR lacks a functional terminal resolution site (trs) and is used for production of self-complementary AAV vectors (scAAV vectors). In some embodiments, a truncated ITR is a ΔITR, for example as described by McCarty et al. (2003) Gene Ther. 10(26):2112-8.

In some aspects, the disclosure relates to recombinant AAVs (rAAVs) comprising a transgene that encodes a nucleic acid as described herein (e.g., an rAAV vector as described herein). The term "rAAVs" generally refers to viral particles comprising an rAAV vector encapsidated by one or more AAV capsid proteins. An rAAV described by the disclosure may comprise a capsid protein having a serotype selected from AAV1, AAV2, AAV3, AAV4, AAV5, AAV6, AAV7, AAV8, AAV9, and AAV10. In some embodiments, an rAAV comprises a capsid protein from a non-human host, for example a rhesus AAV capsid protein such as AAVrh.10, AAVrh.39, etc. In some embodiments, an rAAV described by the disclosure comprises a capsid protein that is a variant of a wild-type capsid protein, such as a capsid protein variant that includes at least 1, 2, 3, 4, 5, 6, 7, 8, 9, 10, or more than 10 (e.g., 15, 20 25, 50, 100, etc.) amino acid substitutions (e.g., mutations) relative to the wild-type AAV capsid protein from which it is derived. In some embodiments, an AAV capsid protein variant is an AAV1RX capsid protein, for example as described by Albright et al. Mol Ther. 2018 Feb. 7; 26(2):510-523. In some embodiments, a capsid protein variant is an AAV TM6 capsid protein, for example as described by Rosario et al. Mol Ther Methods Clin Dev. 2016; 3: 16026.

In some embodiments, rAAVs described by the disclosure readily spread through the CNS, particularly when introduced into the CSF space or directly into the brain parenchyma. Accordingly, in some embodiments, rAAVs described by the disclosure comprise a capsid protein that is capable of crossing the blood-brain barrier (BBB). For example, in some embodiments, an rAAV comprises a capsid protein having an AAV9 or AAVrh.10 serotype. Production of rAAVs is described, for example, by Samulski et al. (1989) J Virol. 63(9):3822-8 and Wright (2009) Hum Gene Ther. 20(7): 698-706. In some embodiments, an rAAV comprises a capsid protein that specifically or preferentially targets myeloid cells, for example microglial cells.

In some embodiments, an rAAV as described by the disclosure (e.g., comprising a recombinant rAAV genome encapsidated by AAV capsid proteins to form an rAAV capsid particle) is produced in a Baculovirus vector expression system (BEVS). Production of rAAVs using BEVS are described, for example by Urabe et al. (2002) Hum Gene Ther 13(16):1935-43, Smith et al. (2009) Mol Ther 17(11): 1888-1896, U.S. Pat. Nos. 8,945,918, 9,879,282, and International PCT Publication WO 2017/184879. However, an rAAV can be produced using any suitable method (e.g., using recombinant rep and cap genes).

Modulation of Gene Expression

Aspects of the disclosure relate to compositions and methods for positively or negatively regulating the expression of a gene therapeutic (e.g., a therapeutic protein expressed from an AAV vector), through the use of certain nucleic acids, for example antisense oligonucleotides (ASOs) that specifically bind (e.g., hybridize) to one or more of the following: viral vector regions (e.g., AAV ITRs), DNA or RNA regulatory elements (e.g., promoter sequences, enhancer sequences, post-transcriptional regulatory element sequences, etc.), and protein coding sequences of mRNA transcribed from rAAV vectors. An isolated nucleic acid may be administered to a cell or subject at the same time as the expression cassette or rAAV vector to which it specifically binds, or at a different time (e.g., before or after administration of the expression cassette or rAAV vector). In some embodiments, a subject is administered an rAAV and then subsequently administered one or more doses of an isolated nucleic acid (or isolated nucleic acids) as described herein. In some embodiments, a subject is administered one or more isolated nucleic acids based upon detecting a level of transgene expression in the cell or subject prior to the administration of the isolated nucleic acids.

In some embodiments, an rAAV vector is in a cell, such as a host cell. A host cell can be a prokaryotic cell or a eukaryotic cell. For example, a host cell can be a mammalian cell, bacterial cell, yeast cell, insect cell, etc. In some embodiments, a host cell is a mammalian cell, for example a HEK293T cell. In some embodiments, a host cell is a bacterial cell, for example an *E. coli* cell. In some embodiments, a cell is in vitro. In some embodiments, a cell is in a subject, for example a mammalian subject such as a human, mouse, dog, cat, etc.

In some embodiments, one isolated nucleic acid that specifically binds to an rAAV vector or expression cassette is provided to a cell or subject. In some embodiments, more than one (e.g., 2, 3, 4, 5, or more) isolated nucleic acids are provided to the cell or subject. The more than one different isolated nucleic acids (e.g., ASOs) may bind to the same region or sequence (e.g., two ASOs that each bind to an AAV ITR), or each to different regions or sequences (e.g., a first ASO that specifically binds to an AAV ITR and a second ASO that binds to a post-transcriptional regulatory element sequence).

Delivery of the one or more isolated nucleic acids described by the disclosure to a cell or subject, in some embodiments, results in modulation (e.g., increase or decrease) in transgene expression caused by binding of the one or more isolated nucleic acids (e.g., ASOs) to a sequence of an rAAV vector or expression construct contained in the cell or subject. In some embodiments, binding of the one or more isolated nucleic acids (e.g., ASOs) to an rAAV vector or expression construct results in an increase in transgene expression of about 1%, 5%, 10%, 20%, 50%, 100%, 500%, 100% or more, relative to transgene expression of an rAAV vector or expression construct that has not been contacted with the one or more isolated nucleic acids. In some embodiments, binding of the one or more isolated nucleic acids (e.g., ASOs) to an rAAV vector or expression construct results in an increase in transduction efficiency of about 1%, 5%, 10%, 20%, 50%, 100%, 500%, 100% or more, relative to transgene expression of an rAAV vector or expression construct that has not been contacted with the one or more isolated nucleic acids. In some embodiments, binding of the one or more isolated nucleic acids (e.g., ASOs) to an rAAV vector or expression construct results in a decrease in transgene expression of about 1%, 5%, 10%, 20%, 50%, 100%, 500%, or 100%, relative to transgene expression of an rAAV vector or expression construct that has not been contacted with the one or more isolated nucleic acids. In some embodiments, the one or more isolated nucleic acid is delivered to the cell at the same time as the cell is transfected with the plasmid comprising the rAAV vector encoding the transgene. In some embodiments, the one or more isolated nucleic acid is delivered to the cell after the cell is transfected with the plasmid comprising the rAAV vector encoding the transgene. In some embodiments, the one or more isolated nucleic acid is delivered to the cell 1, 2, 3, 4, 5, 6, 7, 8, 9, 10, 12, 14, 16, 18, 20, 22 or 24 hours after the cell is transfected with the plasmid comprising the rAAV vector encoding the transgene. In some embodiments, the one or more isolated nucleic acid is delivered to the cell 1, 2, 3, 4, 5, 6, 7, 8, 9, 10, 11, 12, 13, 14, 15, 16, 17, 18, 19 or 20 days after the cell is transfected with the plasmid comprising the rAAV vector encoding the transgene. In some embodiments, the one or more isolated nucleic acid is delivered to the cell 1, 2, 3, 4, 10, 15, 20, 26 or 52 weeks after the cell is transfected with the plasmid comprising the rAAV vector encoding the transgene. In some embodiments, the one or more isolated nucleic acid is delivered to the cell 1, 2, 3 or 5 years after the cell is transfected with the plasmid comprising the rAAV vector encoding the transgene.

Aspects of the disclosure relate to compositions for modulation of expression of one or more CNS disease-associated gene products in a subject to treat CNS-associated diseases. The one or more CNS disease-associated gene products may be encoded by one or more isolated nucleic acids or rAAV vectors. In some embodiments, a subject is administered a single vector (e.g., isolated nucleic acid, rAAV, etc.) encoding one or more (1, 2, 3, 4, 5, or more) gene products. In some embodiments, a subject is administered a plurality (e.g., 2, 3, 4, 5, or more) vectors (e.g., isolated nucleic acids, rAAVs, etc.), where each vector encodes a different CNS disease-associated gene product.

A CNS-associated disease may be a neurodegenerative disease, synucleinopathy, tauopathy, or a lysosomal storage disease. Examples of neurodegenerative diseases and their associated genes are listed in Table 1.

A "synucleinopathy" refers to a disease or disorder characterized by reduced expression or activity of alpha-Synuclein (the gene product of SCNA) in a subject (e.g., relative to a healthy subject, for example a subject not having a synucleinopathy). Examples of synucleinopathies and their associated genes are listed in Table 2.

A "tauopathy" refers to a disease or disorder characterized by reduced expression or activity of Tau protein in a subject (e.g., a healthy subject not having a tauopathy). Examples of tauopathies and their associated genes are listed in Table 3.

A "lysosomal storage disease" refers to a disease characterized by abnormal build-up of toxic cellular products in lysosomes of a subject. Examples of lysosomal storage diseases and their associated genes are listed in Table 4.

TABLE 1

Examples of neurodegenerative diseases

Figure 4:
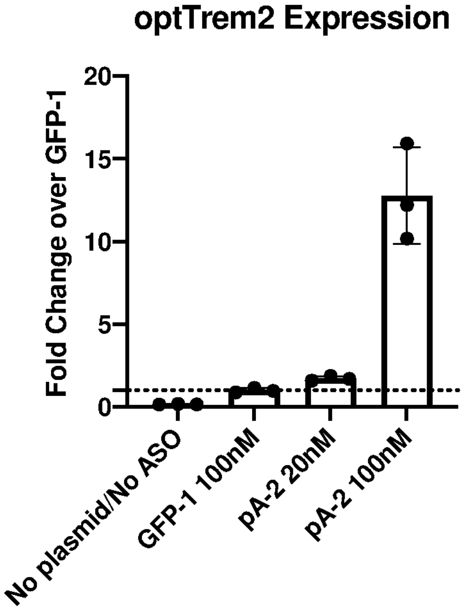
FIG. 4 shows the effects of ASO PolyA ASO-2 on Trem2 expression in HEK293T cells transfected with plasmid encoding Trem2 and with the indicated ASO. Cells were harvested after 72 hours and GBA expression was quantified using qRT-PCR.

| Disease | Associated genes |
|---|---|
| Alzheimer's disease | APP, PSEN1, PSEN2, APOE |
| Parkinson's disease | LRRK2, PARK7, PINK1, PRKN, SNCA, GBA, UCHL1, ATP13A2, VPS35 |
| Huntington's disease | HTT |
| Amyotrophic lateral sclerosis | ALS2, ANG, ATXN2, C9orf72, CHCHD10, CHMP2B, DCTN1, ERBB4, FIG4, FUS, HNRNPA1, MATR3, NEFH, OPTN, PFN1, PRPH, SETX, SIGMAR1, |

TABLE 1-continued

| Examples of neurodegenerative diseases | |
|---|---|
| Disease | Associated genes |
| | SMN1, SOD1, SPG11, SQSTM1, TARDBP, TBK1, TRPM7, TUBA4A, UBQLN2, VAPB, VCP |
| Batten disease (Neuronal ceroid lipofunscinosis) | PPT1, TPP1, CLN3, CLN5, CLN6, MFSD8, CLN8, CTSD, DNAJC5, CTSF, ATP13A2, GRN, KCTD7 |
| Friedreich's ataxia | FXN |
| Lewy body disease | APOE, GBA, SNCA, SNCB |
| Spinal muscular atrophy | SMN1, SMN2 |
| Multiple sclerosis | CYP27B1, HLA-DRB1, IL2RA, IL7R, TNFRSF1A |
| Prion disease (Creutzfeldt-Jakob disease, Fatal familial insomnia, Gertsmann-Straussler-Scheinker syndrome, Variably protease-sensitive prionopathy) | PRNP |

TABLE 2

| Examples of synucleinopathies | |
|---|---|
| Disease | Associated genes |
| Parkinson's disease | LRRK2, PARK7, PINK1, PRKN, SNCA, GBA, UCHL1, ATP13A2, VPS35 |
| Dementia with Lewy bodies | APOE, GBA, SNCA, SNCB |
| Multiple system atrophy | COQ2, SNCA |

TABLE 3

| Examples of tauopathies | |
|---|---|
| Disease | Associated genes |
| Alzheimer's disease | APP, PSEN1, PSEN2, APOE |
| Primary age-related tauopathy | MAPT |
| Progressive supranuclear palsy | MAPT |
| Corticobasal degeneration | MAPT, GRN, C9orf72, VCP, CHMP2B, TARDBP, FUS |
| Frontotemporal dementia with parkinsonism-17 | MAPT |
| Subacute sclerosing panencephalitis | SCN1A |
| Lytico-Bodig disease | |
| Gangioglioma, gangliocytoma | |
| Meningioangiomatosis | |
| Postencephalitic parkinsonism | |
| Chronic traumatic encephalopathy | |

TABLE 4

| Examples of lysosomal storage diseases | |
|---|---|
| Disease | Associated genes |
| Niemann-Pick disease | NPC1, NPC2, SMPD1 |
| Fabry disease | GLA |
| Krabbe disease | GALC |
| Gaucher disease | GBA |
| Tach-Sachs disease | HEXA |
| Metachromatic leukodystrophy | ARSA, PSAP |
| Farber disease | ASAH1 |
| Galactosialidosis | CTSA |
| Schindler disease | NAGA |
| GM1 gangliosidosis | GLB1 |
| GM2 gangliosidosis | GM2A |
| Sandhoff disease | HEXB |
| Lysosomal acid lipase deficiency | LIPA |
| Multiple sulfatase deficiency | SUMF1 |
| Mucopolysaccharidosis Type I | IDUA |
| Mucopolysaccharidosis Type II | IDS |
| Mucopolysaccharidosis Type III | GNS, HGSNAT, NAGLU, SGSH |

TABLE 4-continued

| Examples of lysosomal storage diseases | |
|---|---|
| Disease | Associated genes |
| Mucopolysaccharidosis Type IV | GALNS, GLB1 |
| Mucopolysaccharidosis Type VI | ARSB |
| Mucopolysaccharidosis Type VII | GUSB |
| Mucopolysaccharidosis Type IX | HYAL1 |
| Mucolipidosis Type II | GNPTAB |
| Mucolipidosis Type III alpha/beta | GNPTAB |
| Mucolipidosis Type III gamma | GNPTG |
| Mucolipidosis Type IV | MCOLN1 |
| Neuronal ceroid lipofuscinosis | PPT1, TPP1, CLN3, CLN5, CLN6, MFSD8, CLN8, CTSD, DNAJC5, CTSF, ATP13A2, GRN, KCTD7 |
| Alpha-mannosidosis | MAN2B1 |
| Beta-mannosidosis | MANBA |
| Aspartylglucosaminuria | AGA |
| Fucosidosis | FUCA1 |

As used herein "treat" or "treating" refers to (a) preventing or delaying onset of a CNS disease; (b) reducing severity of a CNS disease; (c) reducing or preventing development of symptoms characteristic of a CNS disease; and/or (d) preventing worsening of symptoms characteristic of a CNS disease in a subject. Symptoms of CNS disease may include, for example, motor dysfunction (e.g., shaking, rigidity, slowness of movement, difficulty with walking, paralysis), cognitive dysfunction (e.g., dementia, depression, anxiety, psychosis), difficulty with memory, emotional and behavioral dysfunction.

A subject is typically a mammal, preferably a human. In some embodiments, a subject is between the ages of 1 month old and 10 years old (e.g., 1 month, 2 months, 3 months, 4, months, months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 3, years, 4 years, 5 years, 6 years, 7 years, 8 years, 9 years, 10 years, or any age therebetween). In some embodiments, a subject is between 2 years old and 20 years old. In some embodiments, a subject is between 30 years old and 100 years old. In some embodiments, a subject is older than 55 years old.

In some embodiments, one or more compositions is administered directly to the CNS of the subject, for example by direct injection into the brain and/or spinal cord of the subject. Examples of CNS-direct administration modalities include but are not limited to intracerebral injection, intraventricular injection, intracisternal injection, intraparenchymal injection, intrathecal injection, and any combination of the foregoing. In some embodiments, direct injection into the CNS of a subject results in transgene expression (e.g., expression of the first gene product, second gene product, and if applicable, third gene product) in the midbrain, striatum and/or cerebral cortex of the subject. In some embodiments, direct injection into the CNS results in transgene expression (e.g., expression of the first gene product, second gene product, and if applicable, third gene product) in the spinal cord and/or CSF of the subject.

In some embodiments, direct injection to the CNS of a subject comprises convection enhanced delivery (CED). Convection enhanced delivery is a therapeutic strategy that involves surgical exposure of the brain and placement of a small-diameter catheter directly into a target area of the brain, followed by infusion of a therapeutic agent (e.g., a composition or rAAV as described herein) directly to the brain of the subject. CED is described, for example by Debinski et al. (2009) Expert Rev Neurother. 9(10):1519-27.

In some embodiments, a composition is administered peripherally to a subject, for example by peripheral injection. Examples of peripheral injection include subcutaneous injection, intravenous injection, intra-arterial injection, intraperitoneal injection, or any combination of the foregoing. In some embodiments, the peripheral injection is intra-arterial injection, for example injection into the carotid artery of a subject.

In some embodiments, a composition (e.g., a composition comprising an isolated nucleic acid or a vector or a rAAV, and/or an isolated nucleic acid as described herein) as described by the disclosure is administered both peripherally and directly to the CNS of a subject. For example, in some embodiments, a subject is administered a composition by intra-arterial injection (e.g., injection into the carotid artery) and by intraparenchymal injection (e.g., intraparenchymal injection by CED). In some embodiments, the direct injection to the CNS and the peripheral injection are simultaneous (e.g., happen at the same time). In some embodiments, the direct injection occurs prior (e.g., between 1 minute and 1 week, or more before) to the peripheral injection. In some embodiments, the direct injection occurs after (e.g., between 1 minute and 1 week, or more after) the peripheral injection.

In some embodiments, a subject is administered an immunosuppressant prior to (e.g., between 1 month and 1 minute prior to) or at the same time as a composition as described herein. In some embodiments, the immunosuppressant is a corticosteroid (e.g., prednisone, budesonide, etc.), an mTOR inhibitor (e.g., sirolimus, everolimus, etc.), an antibody (e.g., adalimumab, etanercept, natalizumab, etc.), or methotrexate.

The amount of composition (e.g., a composition comprising an isolated nucleic acid or a vector or a rAAV) as described by the disclosure administered to a subject will vary depending on the administration method.

A composition (e.g., a composition comprising an isolated nucleic acid or a vector or a rAAV) as described by the disclosure can be administered to a subject once or multiple times (e.g., 2, 3, 4, 5, 6, 7, 8, 9, 10, 20, or more) times. In some embodiments, a composition is administered to a subject continuously (e.g., chronically), for example via an infusion pump.

EXAMPLES

Examples 1-5: Cell Based Assays of Viral Transduction into GBA-Deficient Cells Cells deficient in GBA1 are obtained, for example as fibroblasts from GD patients, monocytes, or hES cells, or patient-derived induced pluripotent stem cells (iPSCs), or HEK293T cells. These cells accumulate substrates such as glucosylceramide and glucosylsphingosine (GlcCer and GlcSph). Treatment of wild-type or mutant cultured cell lines with Gcase inhibitors, such as CBE, is also be used to obtain GBA deficient cells.

The cells are administered an rAAV comprising an AAV9 capsid protein enclosing an rAAV vector comprising the nucleic acid sequences set forth in SEQ ID NOs: 1, 9, 25, 40, 51, and 80 (e.g., PR001). Transduction efficiency and GBA expression level is monitored in the cells. One or more isolated nucleic acids (e.g., ASOs) targeting the PR001 vector are administered to the cell. Therapeutic endpoints (e.g., reduction of PD-associated pathology for in vivo assays) are measured in the context of expression of transduction of the AAV vectors, to confirm and quantify increase or decrease in activity and function of PR001. GBA expression is quantified using qRT-PCT, or through Gcase level measurement using protein ELISA measures, or by standard Gcase activity assays.

Example 1: Effect of ASOs Directed Against GBA

HEK293T cells were transfected with a plasmid comprising an rAAV vector encoding GBA protein (e.g., PR001) and administered ASOs directed against the GBA-encoding portion of the rAAV vector (PR001). The levels and types of ASOs administered in the eight experimental groups were as follows: 20 nM GBA ASO 1 modified (SEQ ID NO: 91), 100 nM GBA ASO 1 modified (SEQ ID NO: 91), 20 nM GBA ASO 2 modified (SEQ ID NO: 92), 100 nM GBA ASO 2 modified (SEQ ID NO: 92), 20 nM GBA ASO 3 modified (SEQ ID NO: 93), 100 nM GBA ASO 3 modified (SEQ ID NO: 93), 20 nM GBA ASO 4 modified (SEQ ID NO: 94), 100 nM GBA ASO 4 modified (SEQ ID NO: 94). A negative control group and a positive control group were also included in the experimental design. In the negative control, cells were not transfected by the GBA-encoding plasmid and were not administered any ASOs. In the positive control, cells were transfected with the plasmid encoding GBA expression and administered 100 nM of an ASO directed against GFP (Green Fluorescent Protein), comprising the nucleic acid sequence set forth in SEQ ID NO: 105. Cells were harvested after 72 hours and GBA expression was quantified using qRT-PCR. All experimental groups showed a significant decrease in GBA expression compared to the positive control (FIG. 1).

Example 2: Effect of ASOs Directed Against WPRE

Figure 2:
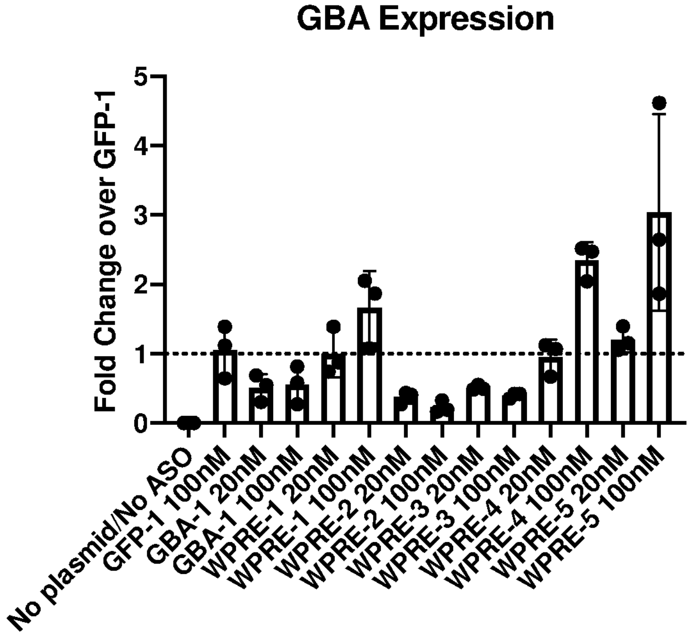
FIG. 2 shows the effects of ASOs directed against WPRE on GBA expression in HEK293T cells transfected with plasmid encoding GBA and with the indicated ASO. Cells were harvested after 72 hours and GBA expression was quantified using qRT-PCR.

HEK293T cells were transfected with a plasmid comprising an rAAV vector encoding GBA protein (e.g., PR001) and administered ASOs directed against the WPRE-encoding portion of the rAAV vector (PR001). The levels and types of ASOs administered in the ten experimental groups were as follows: 20 nM WPRE ASO 1 modified (SEQ ID NO: 96), 100 nM WPRE ASO 1 modified (SEQ ID NO: 96), 20 nM WPRE ASO 2 modified (SEQ ID NO: 97), 100 nM WPRE ASO 2 modified (SEQ ID NO: 97), 20 nM WPRE ASO 3 modified (SEQ ID NO: 98), 100 nM WPRE ASO 3 modified (SEQ ID NO: 98), 20 nM WPRE ASO 4 modified (SEQ ID NO: 99), 100 nM WPRE ASO 4 modified (SEQ ID NO: 99), 20 nM WPRE ASO 5 modified (SEQ ID NO: 100), 100 nM WPRE ASO 5 modified (SEQ ID NO: 100). Four control groups were also included in the experimental design: a negative control group where cells were not transfected by the GBA-encoding plasmid and were not administered any ASOs, a positive control group where cells were transfected with the plasmid encoding GBA expression and administered 100 nM of an ASO directed against GFP (SEQ ID NO: 105), and two groups where cells were transfected with the GBA-encoding plasmid and administered 20 nM GBA ASO 1 modified (SEQ ID NO: 91) and 100 nM GBA ASO 1 modified (SEQ ID NO: 91) respectively. Cells were harvested after 72 hours and GBA expression was quantified using qRT-PCR. Surprisingly, increased GBA expression compared to the positive control was observed in several of the experimental groups, notably the groups that were administered 100 nM of WPRE ASO 1 modified (SEQ ID NO: 96), WPRE ASO 4 modified (SEQ ID NO: 99), or WPRE ASO 5 modified (SEQ ID NO: 100) (FIG. 2).

Example 3: Effect of ASOs Directed Against the Bovine Growth Hormone Poly-Adenylation Element (BGH PolyA)

Figure 3:
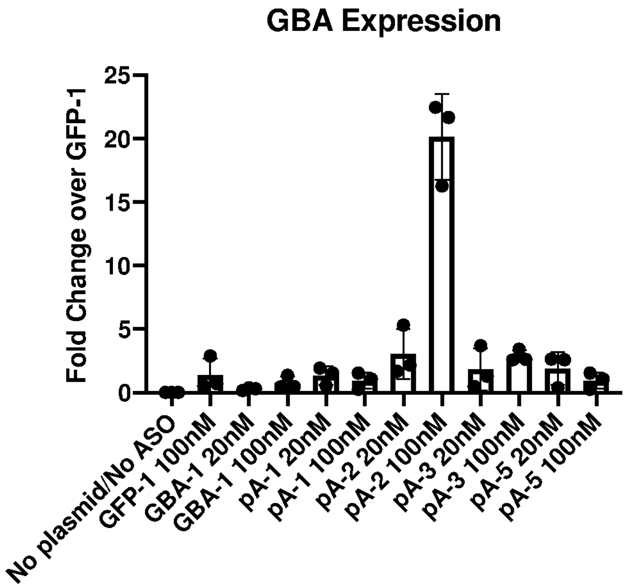
FIG. 3 shows the effects of ASOs directed against BGH PolyA on GBA expression in HEK293T cells transfected with plasmid encoding GBA and with the indicated ASO. Cells were harvested after 72 hours and GBA expression was quantified using qRT-PCR.

HEK293T cells were transfected with a plasmid comprising an rAAV vector encoding GBA protein (e.g., PR001) and administered ASOs directed against the BGH poly-adenylation element (PolyA)-encoding portion of the rAAV vector (PR001). The levels and types of ASOs administered in the eight experimental groups were as follows: 20 nM PolyA ASO 1 modified (SEQ ID NO: 101), 100 nM PolyA ASO 1 modified (SEQ ID NO: 101), 20 nM PolyA ASO 2 modified (SEQ ID NO: 102), 100 nM PolyA ASO 2 modified (SEQ ID NO: 102), 20 nM PolyA ASO 3 modified (SEQ ID NO: 103), 100 nM PolyA ASO 3 modified (SEQ ID NO: 103), 20 nM PolyA ASO 5 modified (SEQ ID NO: 104), 100 nM PolyA ASO 5 modified (SEQ ID NO: 104). Four control groups were also included in the experimental design: a negative control group where cells were not transfected by the GBA-encoding plasmid and were not administered any ASOs, a positive control group where cells were transfected with the plasmid encoding GBA expression and administered 100 nM of an ASO directed against GFP (SEQ ID NO: 105), and two groups where cells were transfected with the GBA-encoding plasmid and administered nM GBA ASO 1 modified (SEQ ID NO: 91) or 100 nM GBA ASO 1 modified (SEQ ID NO: 91) respectively. Cells were harvested after 72 hours and GBA expression was quantified using qRT-PCR. Surprisingly, all experimental groups showed similar or significantly increased GBA expression compared to the positive control. Notably, a 20-fold increase in GBA expression compared to the positive control was observed in the cells that were administered 100 nM of PolyA ASO 2 modified (SEQ ID NO: 102) (FIG. 3).

Example 4: Effect of PolyA ASO 2 Modified (SEQ ID NO: 102) on Trem2 Expression

HEK293T cells were transfected with a plasmid comprising an rAAV vector encoding Trem2 protein and administered 20 nM or 100 nM of PolyA ASO 2 modified (SEQ ID NO: 102), respectively. Two control groups were also included in the experimental design: a negative control group where cells were not transfected by the Trem2-encoding plasmid and were not administered any ASOs, and a positive control group where cells were transfected with the plasmid encoding Trem2 expression and administered 100 nM of an ASO directed against GFP (SEQ ID NO: 105). Cells were harvested after 72 hours and Trem2 expression was quantified using qRT-PCR. Both experimental groups showed a significant increase in Trem2 expression compared to the positive control. Notably, the cells administered 100 nM of PolyA ASO 2 2 modified (SEQ ID NO: 102) showed a 13-fold increase in Trem2 expression compared to the positive control (FIG. 4).

Example 5: Effect of Administering ASOs in Sequential Transfection

Figure 5:
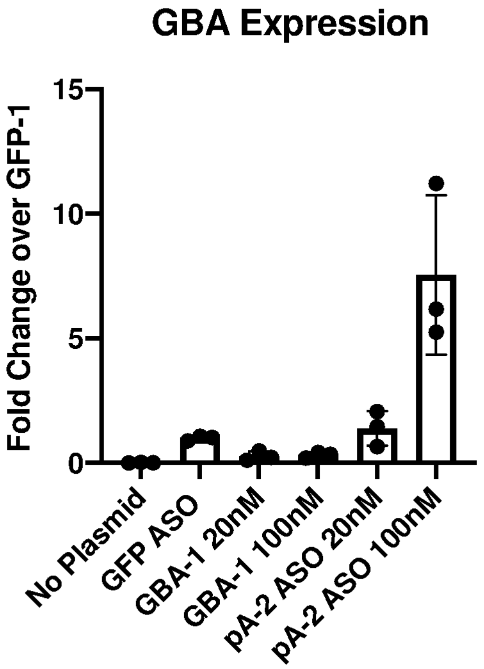
FIG. 5 shows the effects of ASOs in sequential transfection on GBA expression. HEK293T cells were transfected with a plasmid encoding GBA expression. After 3 hours, plasmid transfection mixture was removed and cells were transfected with indicated ASO. Cells were harvested after 72 hours and GBA expression was quantified using qRT-PCR.
Figure 6:
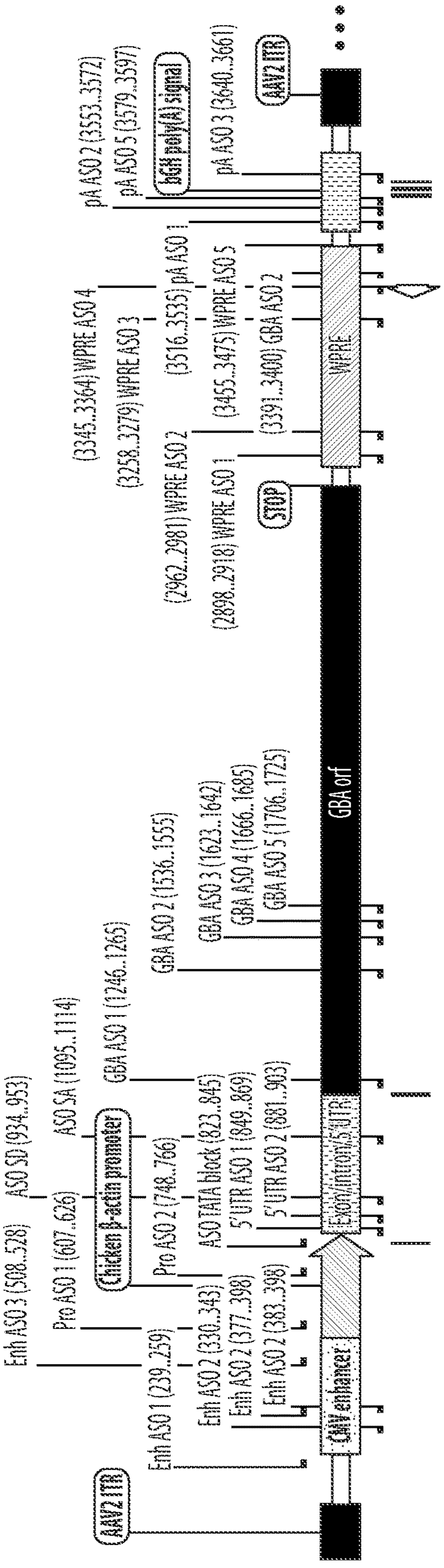
FIG. 6 shows ASO target sequences for the PR001 construct.

HEK293T cells were transfected with a plasmid comprising an rAAV vector encoding GBA protein. After 3 hours, the plasmid transfection mixture was removed and cells in four experimental groups were transfected with: 20 nM GBA ASO 1 modified (SEQ ID NO: 91), 100 nM GBA ASO 1 modified (SEQ ID NO: 91), 20 nM of PolyA ASO 2 modified (SEQ ID NO: 102) or 100 nM of PolyA ASO 2 modified (SEQ ID NO: 102), respectively. Two control groups were also included in the experimental design: a negative control group where cells were not transfected by the GBA-encoding plasmid and were not administered any ASOs, and a positive control group where cells were transfected with the plasmid encoding GBA expression and administered 100 nM of an ASO directed against GFP (SEQ ID NO: 105). Cells were harvested after 72 hours and GBA expression was quantified using qRT-PCR. Both experimental groups that were administered GBA ASO 1 modified (SEQ ID NO: 91) showed a significant decrease in GBA expression compared to the positive control. The group that was administered 20 nM of PolyA ASO 2 modified (SEQ ID NO: 102) showed similar levels of GBA expression as the positive group. The cells that were administered 100 nM of PolyA ASO 2 modified (SEQ ID NO: 102) had the most significant change, with a 7-8 fold increase in GBA expression compared to the positive control (FIG. 5).

Example 6: In Vivo Assays

C57/BL6J male mice received IV infusions of an AAV expressing GBA (AAV-GBA) at $1\times10^{12}$ vg/kg or excipient control. Mice in the excipient group then received saline control, while mice received AAV-GBA then received IV infusions of saline or an ASO 7, 14 and 21 days following AAV-GBA infusion, as detailed in Table 5. Plasma was collected by submandibular bleed before AAV-GBA infusion and 7- and 21-days post AAV-GBA infusion. Mice were euthanized and tissues were collected for analysis 30 days after AAV infusion.

TABLE 5

In vivo assays

| Group | Virus | ASO | ASO dose | N |
|---|---|---|---|---|
| 1 | Excipient | None | n/a | 8 |
| 2 | AAV-GBA | None | n/a | 8 |
| 3 | AAV-GBA | GBA ASO 1 (SEQ ID NO: 91) | 20 mg/kg* | 7 |
| 4 | AAV-GBA | WPRE ASO 2 (SEQ ID NO: 97) | 50 mg/kg | 8 |
| 5 | AAV-GBA | PolyA ASO 2 (SEQ ID NO: 102) | 5 mg/kg* | 5 |

*3 mice from group 3 and 1 mouse from group 5 had a day 7 ASO dose of 50 mg/kg

Figure 7:
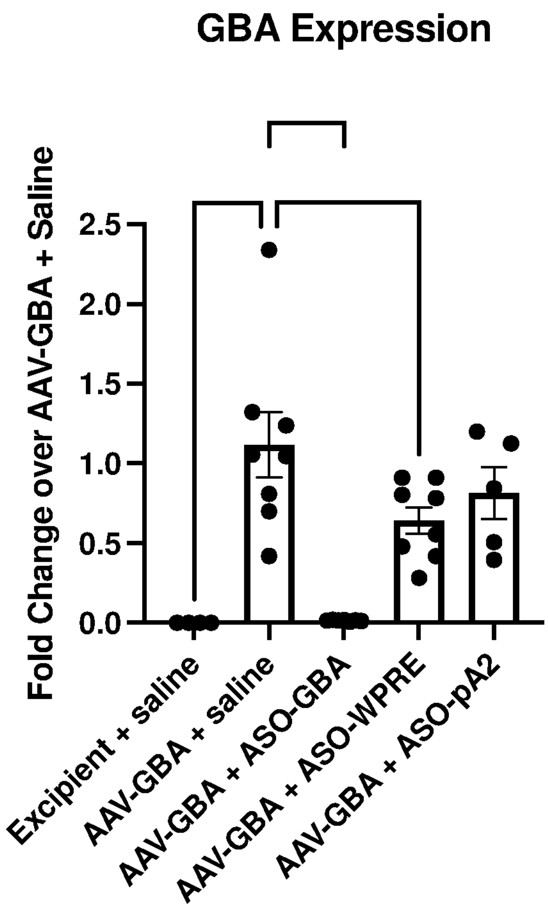
FIG. 7 shows GBA mRNA level in liver of mice received AAV-GBA infusion followed by GBA ASO 1, WPRE ASO 2, or PolyA ASO2 treatment.

The results show that GBA ASO 1 and WPRE ASO 2 significantly decreased GBA mRNA level in the liver, and PolyA ASO 2 showed a trend in decreasing GBA mRNA in the liver (FIG. 7).

In vivo assays of AAV vectors are performed using mutant mice. The intrathecal or intraventricular delivery of vehicle control and AAV vectors (e.g., PR001 at a dose of $2\times10^{11}$ vg/mouse) are performed using concentrated AAV stocks, for example at an injection volume between 5-10 μL. Intraparenchymal delivery by convection enhanced delivery is performed. One or more isolated nucleic acids (e.g., ASOs) targeting the PR001 vector are administered to the cell. Therapeutic endpoints (e.g., reduction of PD-associated pathology) are measured in the context of expression of transduction of the AAV vectors, to confirm and quantify increase or decrease in activity and function of PR001. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

SEQUENCES

In some embodiments, an isolated nucleic acid described herein (e.g., an ASO) specifically binds (e.g., hybridizes) to a sequence set forth below, or the complement thereof, or the reverse complement thereof. In some embodiments, an isolated nucleic acid described herein (e.g., an ASO) comprises or consists of one of the sequences set forth below, or the complement thereof, or the reverse complement thereof, or a gapmer thereof, or a modified version thereof that comprises one or more chemical modifications, wherein the one or more chemical modification is selected from a nucleobase modification or a backbone modification. In some embodiments, all the nucleobases and/or the entire backbone of the ASO are modified. In some embodiments, a nucleobase modification comprises a 2'-O-methyl (2'OMe) modification, and a backbone modification comprises a phosphorothioate linkage. In some embodiments, an ASO comprises one or more locked nucleic acids (LNAs). In the sequences set forth below, the letter "m" preceding a nucleobase letter indicates a 2'-O-methyl (2'OMe) modification, and a "*" between two nucleobases indicates a phosphorothioate linkage.

```
>AAV2 ITR nucleic acid sequence
                                             (SEQ ID NO: 1)
cctgcaggcagctgcgcgctcgctcgctcactgaggccgcccgggcaaag

cccgggcgtcgggcgacctttggtcgcccggcctcagtgagcgagcgagc

gcgcagagagggagtggccaactccatcactaggggttcct

>ITR ASO 1
                                             (SEQ ID NO: 2)
gcgcgcagctgcctgcagg

>ITR ASO 2
                                             (SEQ ID NO: 3)
cggcctcagtgagcgagcga

>ITR ASO 3
                                             (SEQ ID NO: 4)
acgcccgggctttgcccggg

>ITR ASO 4
                                             (SEQ ID NO: 5)
cgggcgaccaaaggtcgcccg

>ITR ASO 5
                                             (SEQ ID NO: 6)
gctcgctcgctcactgaggc

>ITR ASO 6
                                             (SEQ ID NO: 7)
tggccactccctctctgcgc
```

-continued

```
>ITR ASO 7
                                             (SEQ ID NO: 8)
aggaacccctagtgatggagt

>CMV Enhancer nucleic acid sequence
                                             (SEQ ID NO: 9)
cgttacataacttacggtaaatggcccgcctggctgaccgcccaacgacc

cccgcccattgacgtcaataatgacgtatgttcccatagtaacgccaata

gggactttccattgacgtcaatgggtggagtatttacggtaaactgccca

cttggcagtacatcaagtgtatcatatgccaagtacgccccctattgacg

tcaatgacggtaaatggcccgcctggcattatgcccagtacatgacctta

tgggactttcctacttggcagtacatctacgtattagtcatcgctattac

catg

>CMV ASO 1
                                             (SEQ ID NO: 10)
tttaccgtaagttatgtaacg

>CMV ASO 2
                                             (SEQ ID NO: 11)
ggcggtcagccaggcgggcca

>CMV ASO 3
                                             (SEQ ID NO: 12)
gtcaatgggcgggggtcgttg

>CMV ASO 4
                                             (SEQ ID NO: 13)
ggaacatacgtcattattgac

>CMV ASO 5
                                             (SEQ ID NO: 14)
gtccctattggcgttactatg

>CMV ASO 6
                                             (SEQ ID NO: 15)
acccattgacgtcaatggaaa

>CMV ASO 7
                                             (SEQ ID NO: 16)
gcagtttaccgtaaatactcc

>CMV ASO 8
                                             (SEQ ID NO: 17)
acttgatgtactgccaagtgg

>CMV ASO 9
                                             (SEQ ID NO: 18)
ggcgtacttggcatatgatac

>CMV ASO 10
                                             (SEQ ID NO: 19)
ccgtcattgacgtcaataggg

>CMV ASO 11
                                             (SEQ ID NO: 20)
taatgccaggcgggccattta

>CMV ASO 12
                                             (SEQ ID NO: 21)
cataaggtcatgtactgggca

>CMV ASO 13
                                             (SEQ ID NO: 22)
tactgccaagtaggaaagtcc

>CMV ASO 14
                                             (SEQ ID NO: 23)
gcgatgactaatacgtagatg

>CMV ASO 15
                                             (SEQ ID NO: 24)
ccatggtaatagcgatgac
```

-continued

>CBA promoter nucleic acid sequence
(SEQ ID NO: 25)
tcgaggtgagccccacgttctgcttcactctccccatctcccccccctcc
ccacccccaattttgtatttatttattttttaattattttgtgcagcgat
gggggcgggggggggggggggcgcgcgccaggcggggcggggcggggcg
aggggcggggcggggcgaggcggagaggtgcggcggcagccaatcagagc
ggcgcgctccgaaagtttccttttatggcgaggcggcggcggcggcggcc
ctataaaaagcgaagcgcgcggcgggcg >CB ASO 1
(SEQ ID NO: 26)
agaacgtggggctcacctcga >CB ASO 2
(SEQ ID NO: 27)
gggagatggggagagtgaagc >CB ASO 3
(SEQ ID NO: 28)
aaattgggggtggggaggggg >CB ASO 4
(SEQ ID NO: 29)
attaaaaaataaataaataca >CB ASO 5
(SEQ ID NO: 30)
cccccatcgctgcacaaaata >CB ASO 6
(SEQ ID NO: 31)
cgcgcccccccccccccccg >CB ASO 7
(SEQ ID NO: 32)
cccgccccgccccgcctggcg >CB ASO 8
(SEQ ID NO: 33)
tcgccccgccccgcccctcgc >CB ASO 9
(SEQ ID NO: 34)
ctgccgccgcacctctccgcc >CB ASO 10
(SEQ ID NO: 35)
ggagcgcgccgctctgattgg >CB ASO 11
(SEQ ID NO: 36)
tcgccataaaaggaaactttc >CB ASO 12
(SEQ ID NO: 37)
agggccgccgccgccgccgcc >CB ASO 13
(SEQ ID NO: 38)
gccgcgcgcttcgctttttat >CB ASO 14
(SEQ ID NO: 39)
agcgcgcagcgactcccgccc >GBA codon-optimized nucleic acid sequence
(SEQ ID NO: 40)
auggaauucagcagccccagcagagaggaaugccccaagccucugagccg
ggugucaaucauggccggaucucugacaggacugcugcugcuucaggccg
ugucuugggcuucuggcgcuagaccuugcauccccaagagcuucggcuac
agcagcgucgugugcgugugcaaugccaccuacugcgacagcuucgaccc
uccuaccuuuccugcucugggcaccuucagcagauacgagagcaccagau
ccggcagacggauggaacugagcaugggacccauccaggccaaucacaca
ggcacuggccugcugcugacacugcagccugagcagaaauuccagaaagu
gaaaggcuucggcggagccaugacagaugccgccgcucugaauauccugg
cucugucuccaccagcucagaaccugcugcucaagagcuacuucagcgag
gaaggcaucggcuacaacaucaucagagugcccauggccagcugcgacuu
cagcaucaggaccuacaccuacgccgacacacccgacgauuuccagcugc
acaacuucagccugccugaagaggacaccaagcugaagaucccucugauc
cacagagcccugcagcuggcacaaagacccgugucacugcuggccucucc
auggacaucucccaccuggcugaaaacaaauggcgccgugaauggcaagg
gcagccugaaaggccaaccuggcgacaucuaccaccagaccugggccaga
uacuucgugaaguuccuggacgccuaugccgagcacaagcugcaguuuug
ggccgugacagccgagaacgaaccuucugcuggacugcugagcggcuacc
ccuuucagugccugggcuuuacacccgagcaccaggggacuuuaucgccc
gugaucugggacccacacuggccaauagcacccaccauaaugugcggcug
cugaugcuggacgaccagagacugcuucugccccacugggcuaaaguggu
gcugacagauccugaggccgccaaauacgugcacggaaucgccgugcacu
gguaucuggacuuucuggccccugccaaggccacacugggagagacacac
agacuguuccccaacaccaugcuguucgccagcgaagccuguguggggcag
caaguuuugggaacagagcgugcggcucggcagcugggauagaggcaugc
aguacagccacagcaucaucaccaaccugcuguaccacgucgucggcugg
accgacuggaaucuggcccugaauccugaaggggcccuaacugggucega
aacuucguggacagccccaucaucguggacaucaccaaggacaccuucua
caagcagcccauguucuaccaccugggacacuucagcaaguucaucccccg
agggcucucagcgcguuggacugguggcuucccagaagaacgaucuggac
gccguggcucugaugcacccugauggaucugcugugguggugguccugaa
ccgcagcagcaaagaugugccccugaccaucaaggaucccgccgugggau
uccuggaaacaaucagcccuggcuacuccauccacaccuaccuguggcgu
agacaguga >GBA ASO 1
(SEQ ID NO: 41)
gcugcugaauuccauggugge >GBA ASO 2
(SEQ ID NO: 42)
ggggcauuccucucugcuggg >GBA ASO 3
(SEQ ID NO: 43)
ugacacccggcucagaggcuu >GBA ASO 4
(SEQ ID NO: 44)
ugucagagauccggccaugau >GBA ASO 5
(SEQ ID NO: 45)
ggccugaagcagcagcagucc >GBA ASO 6
(SEQ ID NO: 46)
agcgccagaagcccaagacac -continued >GBA ASO 7
(SEQ ID NO: 47)
gcucuuggggaugcaaggucu >GBA ASO 8
(SEQ ID NO: 48)
cacgacgcugcuguagccgaa >GBA ASO 9
(SEQ ID NO: 49)
guagguggcauugcacacgca >GBA ASO 10
(SEQ ID NO: 50)
aggagggucgaagcugucgca >WPRE nucleic acid sequence
(SEQ ID NO: 51)
Aaucaaccucuggauuacaaaauuugugaaagauugacugguauucuuaa
cuauguugcuccuuuuaccuauguggauacgcugcuuuaaugccuuugua
ucauguauugcuuccguaugguuuuuuuuuucucuuuaugaggaguugu
ggcccguugucaggcaacguggcguggugugcacuguguuugcugacgca
acccccacugguuggggcauugccaccaccugucagcuccuuuccgggac
uuucgcuuuccccucccuauugccacggggaacucaucgccgccugccu
ugcccgcugcuggacaggggcucggcuguugggcacugacaauuccgugg
uguugucggggaaaucaucguccuuuccuuggcugcucgccuguguugcc
accuggauucugggggacguccuucuguacgucccuucggcccucaaucc
agccuuugggccgccuccccgc >WPRE ASO 1
(SEQ ID NO: 52)
uuuguaauccagagguugauu >WPRE ASO 2
(SEQ ID NO: 53)
accagucaaucuuucacaaau >WPRE ASO 3
(SEQ ID NO: 54)
aggagcaacauaguuaagaau >WPRE ASO 4
(SEQ ID NO: 55)
agcguauccacauagcguaaa >WPRE ASO 5
(SEQ ID NO: 56)
augauacaaaggcauuaaagc >WPRE ASO 6
(SEQ ID NO: 57)
agccauacgggaagcaauagc >WPRE ASO 7
(SEQ ID NO: 58)
auacaaggaggagaaaaugaa >WPRE ASO 8
(SEQ ID NO: 59)
aagagacagcaaccaggauuu >WPRE ASO 9
(SEQ ID NO: 60)
aacgggccacaacuccucaua >WPRE ASO 10
(SEQ ID NO: 61)
caccacgccacguugccugac >WPRE ASO 11
(SEQ ID NO: 62)
ugcgucagcaaacacagugca -continued >WPRE ASO 12
(SEQ ID NO: 63)
aaugccccaaccagugggggu >WPRE ASO 13
(SEQ ID NO: 64)
aaggagcugacagguggguggc >WPRE ASO 14
(SEQ ID NO: 65)
ggggaaagcgaaagucccgga >WPRE ASO 15
(SEQ ID NO: 66)
uuccgccguggcaauagggag >WPRE ASO 16
(SEQ ID NO: 67)
ggcaaggcaggcggcgaugag >WPRE ASO 17
(SEQ ID NO: 68)
ccgagccccuguccagcagcg >WPRE ASO 18
(SEQ ID NO: 69)
ggaauugucagugcccaacag >WPRE ASO 19
(SEQ ID NO: 70)
ugauuuccccgacaacaccac >WPRE ASO 20
(SEQ ID NO: 71)
gagcagccaaggaaaggacga >WPRE ASO 21
(SEQ ID NO: 72)
aauccagguggcaacacaggc >WPRE ASO 22
(SEQ ID NO: 73)
gcagaaggacgucccgcgcag >WPRE ASO 23
(SEQ ID NO: 74)
auugagggccgaagggacgua >WPRE ASO 24
(SEQ ID NO: 75)
gcgggaaggaagguccgcugg >WPRE ASO 25
(SEQ ID NO: 76)
ccgcagagccggcagcaggcc >WPRE ASO 26
(SEQ ID NO: 77)
aaggcgaagacgcggaagagg >WPRE ASO 27
(SEQ ID NO: 78)
gauccgacucgucugagggcg >WPRE ASO 28
(SEQ ID NO: 79)
cggggaggcggcccaaaggga > Bovine growth hormone poly-adenylation addition element
(SEQ ID NO: 80)
cugugccuucuaguugccagccaucuguuuuugcccucccccgugccuuc
cuugacccuggaaggugccacucccacuguccuuuccuaauaaaaugagg
aaauugcaucgcauugucugaguaggugucauucuauucugggggguggg
gggggcaggacagcaaggggggaggauugggaagacaauagcaggcaugcu
gggga -continued >PolyA ASO 1
(SEQ ID NO: 81)
gcuggcaacuagaaggcacag >PolyA ASO 2
(SEQ ID NO: 82)
gggaggggcaaacaacagaug >PolyA ASO 3
(SEQ ID NO: 83)
ccagggucaaggaaggcacgg >PolyA ASO 4
(SEQ ID NO: 84)
ggacagugggaguggcaccuu >PolyA ASO 5
(SEQ ID NO: 85)
uuuccucauuuuauuaggaaa >PolyA ASO 6
(SEQ ID NO: 86)
uacucagacaaugcgaugcaa >PolyA ASO 7
(SEQ ID NO: 87)
cccccagaauagaaugacacc >PolyA ASO 8
(SEQ ID NO: 88)
ugcuguccugccccaccccac >PolyA ASO 9
(SEQ ID NO: 89)
ugucuucccaauccucccccu >PolyA ASO 10
(SEQ ID NO: 90)
ucuccccagcaugccugcuau >GBA ASO 1 modified
(SEQ ID NO: 91)
mG*mG*mG*mG*mC*A*T*T*C*C*T*C*T*C*T*mG*mC*mU*mG*mG >GBA ASO 2 modified
(SEQ ID NO: 92)
mU*mG*mC*mA*mG*T*G*T*C*A*G*C*A*G*C*mA*mG*mG*mC*mC >GBA ASO 3 modified
(SEQ ID NO: 93)
mG*mG*mU*mG*mG*A*G*A*C*A*G*A*G*C*C*mA*mG*mG*mA*mU >GBA ASO 4 modified
(SEQ ID NO: 94)
mG*mC*mC*mU*mU*C*C*T*C*G*C*T*G*A*A*mG*mU*mA*mG*mC >GBA ASO 5 modified
(SEQ ID NO: 95)
mC*mG*mC*mA*mG*C*T*G*G*C*C*A*T*G*G*mG*mC*mA*mC*mU >WPRE ASO 1 modified
(SEQ ID NO: 96)
mC*mU*mU*mU*mC*A*C*A*A*A*T*T*T*T*G*T*mA*mA*mU*
mC*mC >WPRE ASO 2 modified
(SEQ ID NO: 97)
mG*mG*mC*mA*mU*T*A*A*A*G*C*A*G*C*G*mU*mA*mU*mC*mC >WPRE ASO 3 modified
(SEQ ID NO: 98)
mC*mC*mC*mC*mG*A*C*A*A*C*A*C*C*A*C*G*G*mA*mA*mU*
mU*mG >WPRE ASO 4 modified
(SEQ ID NO: 99)
mG*mG*mG*mC*mC*G*A*A*G*G*G*A*C*G*T*mA*mG*mC*mA*mG -continued >WPRE ASO 5 modified
(SEQ ID NO: 100)
mG*mC*mG*mG*mG*G*A*G*G*C*G*G*C*C*C*A*mA*mA*mG*mG*
mG >PolyA ASO 1 modified
(SEQ ID NO: 101)
mG*mG*mC*mU*mG*G*C*A*A*C*T*A*G*A*A*mG*mG*mC*mA*mC >PolyA ASO 2 modified
(SEQ ID NO: 102)
mG*mG*mU*mC*mA*A*G*G*A*A*G*G*C*A*C*mG*mG*mG*mG*mG >PolyA ASO 3 modified
(SEQ ID NO: 103)
mC*mC*mC*mC*mC*C*A*G*A*A*T*A*G*A*A*T*G*mA*mC*mA*
mC*mC >PolyA ASO 5 modified
(SEQ ID NO: 104)
mG*mG*mA*mC*mA*mG*mU*mG*mG*mG*mA*mG*mU*mG*mG*mC*
mA*mC*mC >GFP ASO 1 modified
(SEQ ID NO: 105)
mU*mG*mU*mG*mG*C*C*G*T*T*T*A*C*G*T*mC*mG*mC*mC*mG >GBA ASO 1 unmodified
(SEQ ID NO: 106)
Ggggcauuccucucugcugg >GBA ASO 2 unmodified
(SEQ ID NO: 107)
ugcagugucagcagcaggcc >GBA ASO 3 unmodified
(SEQ ID NO: 108)
gguggagacagagccaggau >GBA ASO 4 unmodified
(SEQ ID NO: 109)
gccuuccucgcugaaguagc >GBA ASO 5 unmodified
(SEQ ID NO: 110)
cgcagcuggccaugggcacu >WPRE ASO 1 unmodified
(SEQ ID NO: 111)
Cuuucacaaauuuuguaaucc >WPRE ASO 2 unmodified
(SEQ ID NO: 112)
Ggcauuaaagcagcguaucc >WPRE ASO 3 unmodified
(SEQ ID NO: 113)
Ccccgacaacaccacggaauug >WPRE ASO 4 unmodified
(SEQ ID NO: 114)
Gggccgaagggacguagcag >WPRE ASO 5 unmodified
(SEQ ID NO: 115)
Gcggggaggcggcccaaaggg >PolyA ASO 1 unmodified
(SEQ ID NO: 116)
ggcuggcaacuagaaggcac >PolyA ASO 2 unmodified
(SEQ ID NO: 117)
ggucaaggaaggcacggggg >PolyA ASO 3 unmodified
(SEQ ID NO: 118)
ccccccagaauagaaugacacc -continued >PolyA ASO 4 unmodified (SEQ ID NO: 119)

ccauagagcccaccgcaucccc

-continued

>PolyA ASO 5 unmodified (SEQ ID NO: 120)

ggacagugggaguggcacc

What is claimed is:

1. A method for modulating expression of a transgene in a cell, comprising contacting the cell with one or more antisense oligonucleotides (ASOs), wherein the cell contains a recombinant adeno-associated virus (AAV) (rAAV) vector comprising a transgene flanked by AAV2 inverted terminal repeats (ITRs), wherein the one or more ASOs specifically bind to at least one of the AAV2 ITRs, and wherein the one or more ASOs comprise a nucleic acid sequence set forth in any one of SEQ ID NOs: 2-8, wherein binding of the one or more ASOs to the AAV2 ITR results in altered expression of the transgene in the cell relative to expression of the transgene in a cell that does not contain the one or more ASOs.

2. The method of claim 1, wherein each of the one or more ASOs comprises one or more chemical modification.

3. The method of claim 2, wherein each of the one or more chemical modifications is selected from a nucleobase modification or a backbone modification.

4. The method of claim 3, wherein all the nucleobases and/or the entire backbone of each of the ASOs are modified.

5. The method of claim 3, wherein the nucleobase modification comprises a 2'-O-methyl (2'OMe) modification.

6. The method of claim 3, wherein the backbone modification comprises a phosphorothioate linkage.

7. The method of claim 3, wherein an ASO comprises one or more locked nucleic acids (LNAs).

8. The method of claim 1, wherein the cell is in a subject.

9. The method of claim 1, wherein the transgene is a therapeutic protein.

10. A method for modulating expression of a transgene in a cell, comprising contacting the cell with one or more antisense oligonucleotides (ASOs), wherein the cell contains a recombinant adeno-associated virus (AAV) (rAAV) vector comprising a transgene;

wherein the one or more ASOs specifically bind to a transcriptional control region sequence of the transgene or a protein coding region of a messenger ribonucleic acid (mRNA) transcribed from the transgene;

wherein (i) the one or more ASOs specifically bind to a transcriptional control region sequence encoding a human cytomegalovirus (CMV) enhancer, and wherein the one or more ASOs comprise a nucleic acid sequence set forth in any one of SEQ ID NOs: 11-24; or (ii) the one or more ASOs specifically bind to a transcriptional control region sequence encoding a chicken B-actin (CBA) promoter, and wherein the one or more ASOs comprise a nucleic acid sequence set forth in any one of SEQ ID NOs: 26-39; and wherein binding of the one or more ASOs to the transcriptional control region sequence or the protein coding region results in altered expression of the transgene in the cell relative to expression of the transgene in a cell that does not contain the one or more ASOs.

11. A method for modulating expression of a transgene in a cell, comprising contacting the cell with one or more antisense oligonucleotides (ASOs), wherein the cell contains a recombinant adeno-associated virus (AAV) (rAAV) vector comprising a transgene with one or more antisense oligonucleotides (ASOs);

wherein (i) the one or more ASOs specifically bind to a woodchuck post-translational regulatory element (WPRE), and wherein the one or more ASOs comprise a nucleic acid sequence set forth in any one of SEQ ID NOs: 53-79, 96-100, or 111-115; or (ii) wherein the one or more ASOs specifically bind to a polyadenylation element of an mRNA transcribed from the transgene, and wherein the one or more ASOs comprises a nucleic acid sequence set forth in any one of SEQ ID NOs: 81-90, 101-104, or 116-120; and wherein binding of the one or more ASOs to the WPRE or the polyadenylation element results in altered expression of the transgene in the cell relative to expression of the transgene in a cell that does not contain the one or more ASOs.

12. A method for modulating expression of a transgene in a cell, comprising contacting the cell with one or more antisense oligonucleotides (ASOs), wherein the cell contains a recombinant adeno-associated virus (AAV) (rAAV) vector comprising a transgene with one or more antisense oligonucleotides (ASOs);

wherein the transgene comprises a nucleotide sequence encoding β-glucocerebrosidase (GBA);

wherein the one or more ASOs specifically bind to the nucleotide sequence encoding GBA, and wherein the one or more ASOs comprise a nucleic acid sequence set forth in any one of SEQ ID NOs: 41-50, 91-95, or 106-110; and wherein binding of the one or more ASOs to the nucleotide sequence encoding GBA results in altered expression of GBA in the cell relative to expression of GBA in a cell that does not contain the one or more ASOs.

* * * * *